(12) United States Patent
Esanu

(10) Patent No.: US 9,259,232 B2
(45) Date of Patent: Feb. 16, 2016

(54) SURGICAL ENDOSCOPIC DEVICE WITH DETACHABLE END TOOL AS A CLAMP

(76) Inventor: Catalin Esanu, Reghin (RO)

( * ) Notice: Subject to any disclaimer, the term of this patent is extended or adjusted under 35 U.S.C. 154(b) by 140 days.

(21) Appl. No.: 13/638,693

(22) PCT Filed: Mar. 29, 2011

(86) PCT No.: PCT/RO2011/000011
§ 371 (c)(1),
(2), (4) Date: Oct. 1, 2012

(87) PCT Pub. No.: WO2012/021082
PCT Pub. Date: Feb. 16, 2012

(65) Prior Publication Data
US 2013/0023911 A1 Jan. 24, 2013

(30) Foreign Application Priority Data
Apr. 2, 2010 (RO) .................................. 10-0309

(51) Int. Cl.
*A61B 17/29* (2006.01)
*A61B 17/122* (2006.01)
*A61B 17/128* (2006.01)
*A61B 18/14* (2006.01)

(52) U.S. Cl.
CPC .............. *A61B 17/29* (2013.01); *A61B 17/122* (2013.01); *A61B 17/1285* (2013.01); *A61B 18/1445* (2013.01); *A61B 2017/292* (2013.01); *A61B 2017/2931* (2013.01); *A61B 2017/2946* (2013.01); *A61B 2018/1432* (2013.01)

(58) Field of Classification Search
CPC ................. A61B 17/122; A61B 17/29; A61B 2017/2901; A61B 2017/2902; A61B 2017/2903; A61B 2017/2909; A61B 2017/2911; A61B 2017/2912; A61B 2017/2919; A61B 2017/292; A61B 2017/2931; A61B 2017/2932; A61B 2017/294; A61B 2017/2943; A61B 2017/2946; A61B 18/1442; A61B 18/1445; A61B 18/1447
USPC ........... 606/157, 158, 170, 174, 184, 185, 40, 606/37, 41, 51, 52, 49, 205–208, 167, 45, 606/46; 81/342; 294/16; 29/267; 30/165, 30/173, 194, 244, 245, 249, 250, 251
See application file for complete search history.

(56) References Cited

U.S. PATENT DOCUMENTS

| | | | |
|---|---|---|---|
| 4,957,500 A | 9/1990 | Liang | |
| 5,026,379 A | 6/1991 | Yoon | |
| 5,242,456 A * | 9/1993 | Nash et al. | .................... 606/142 |
| 5,304,183 A | 4/1994 | Gourlay | |
| 5,792,165 A * | 8/1998 | Klieman et al. | ............... 606/170 |
| 5,827,323 A * | 10/1998 | Klieman et al. | ............... 606/205 |
| 5,921,996 A | 7/1999 | Sherman | |
| 6,210,418 B1 | 4/2001 | Storz | |

(Continued)

Primary Examiner — Jocelin Tanner

(57) ABSTRACT

A surgical endoscopic instrument with detachable end tool as a clamp is provided. The instrument comprises a clamp, removably connected by a coupling to an elongated shaft, this comprising two concentric tubes, which can rotate about each other, connected to a rotating element, that is attached to a housing, inside which a push-pull rod, driven by a handle, transmits the surgeon's commands, leading to the actuating of the end tool's jaws, as well as the clamp detachment/retrieving, from/to the elongated shaft, by operating the coupling, given by the rotation of the concentric tubes about each other, thus resulting in the detachment/attachment of clamp with its jaws blocked in its given position at the time of detachment.

3 Claims, 20 Drawing Sheets

(56) References Cited

U.S. PATENT DOCUMENTS

| | | | |
|---|---|---|---|
| 6,723,109 B2 * | 4/2004 | Solingen | 606/151 |
| 2001/0049540 A1 | 12/2001 | Santilli | |
| 2008/0004656 A1 * | 1/2008 | Livneh | 606/205 |
| 2011/0152895 A1 | 6/2011 | Nyull | |

* cited by examiner

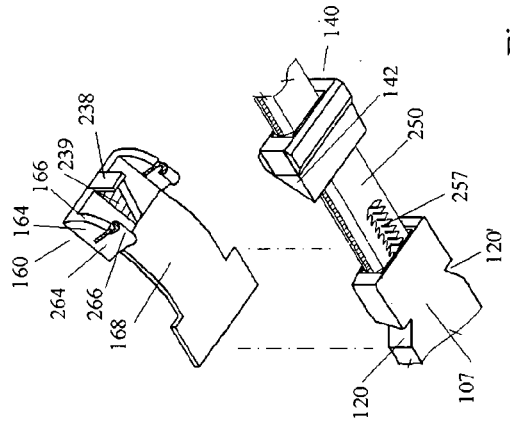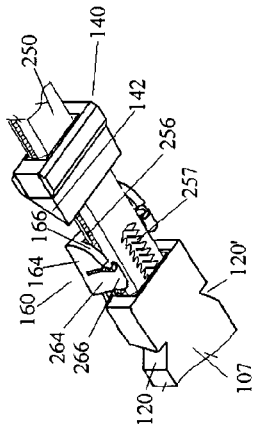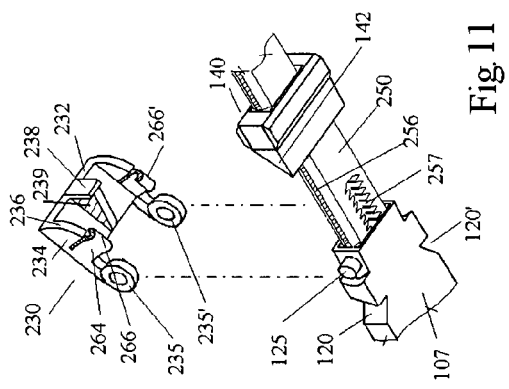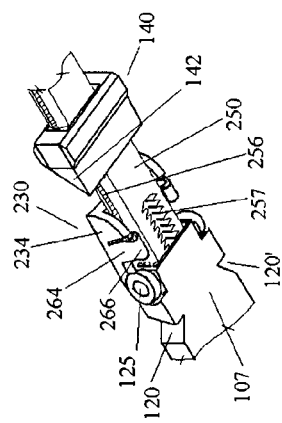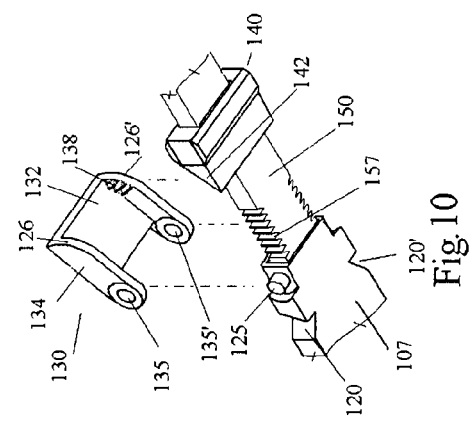

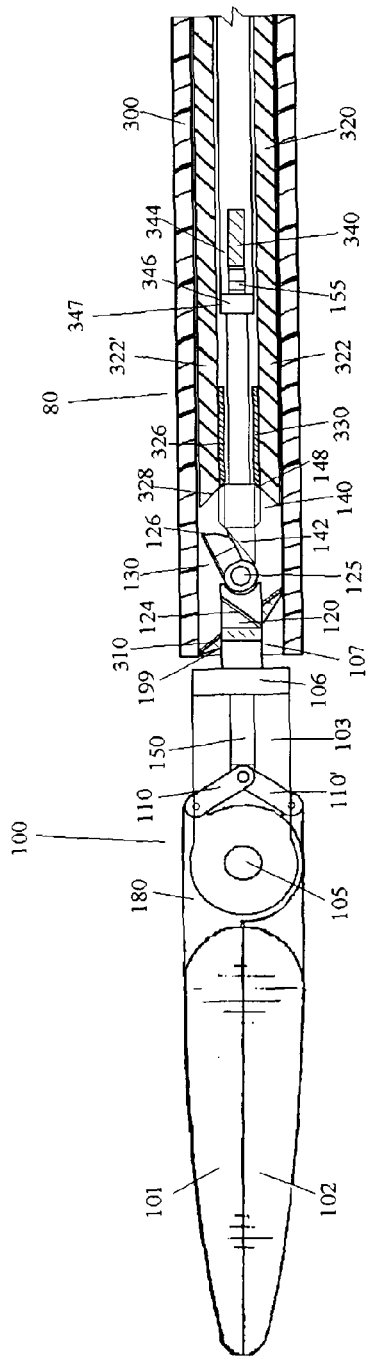
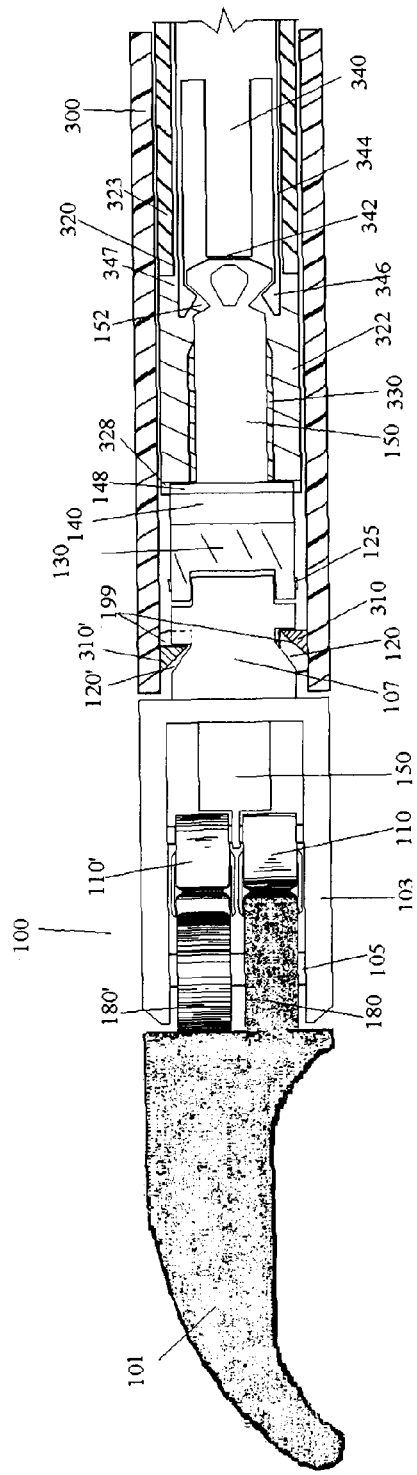
Fig. 16
Fig. 17

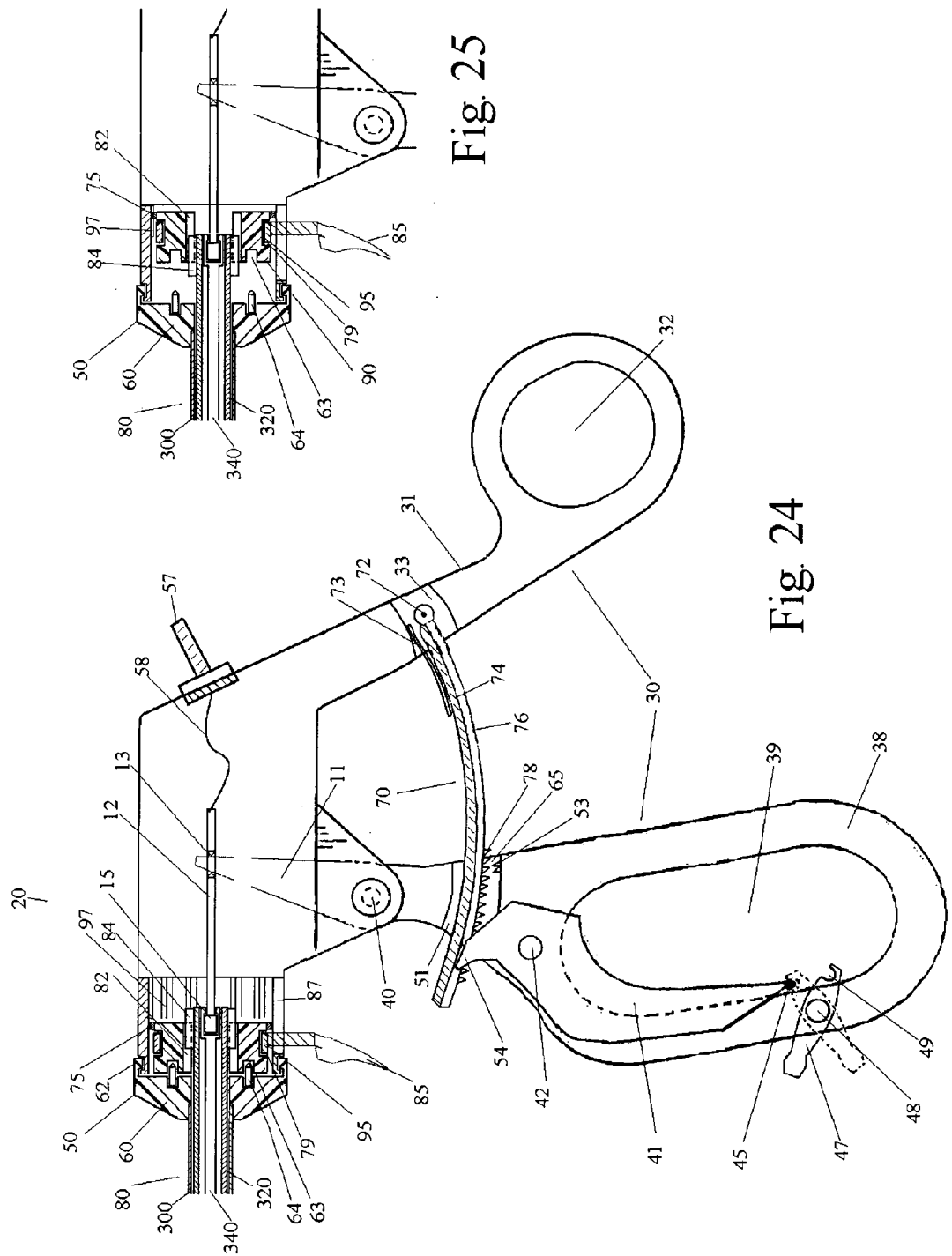

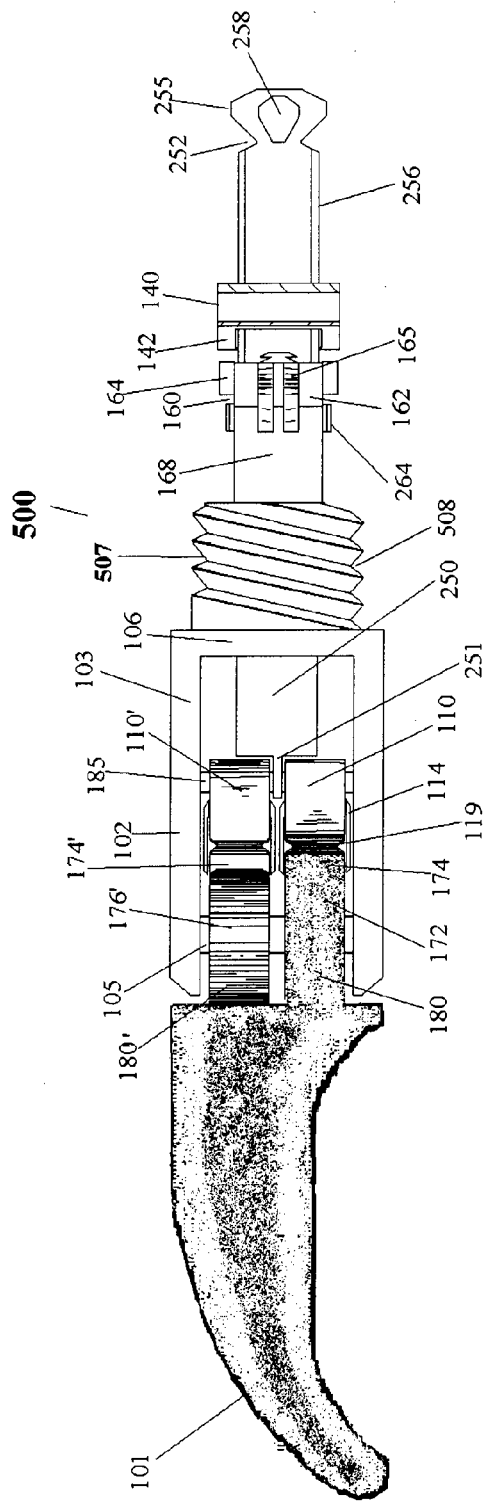
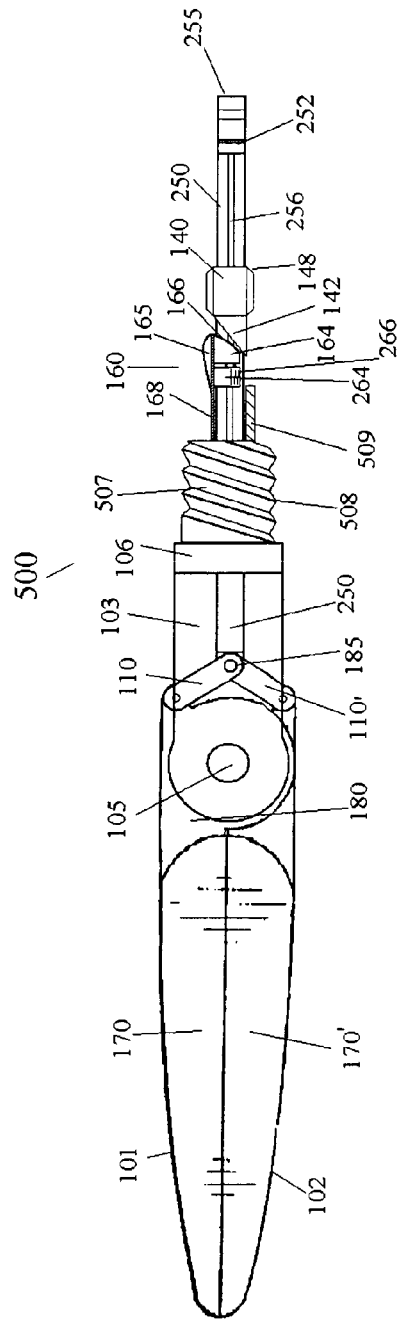

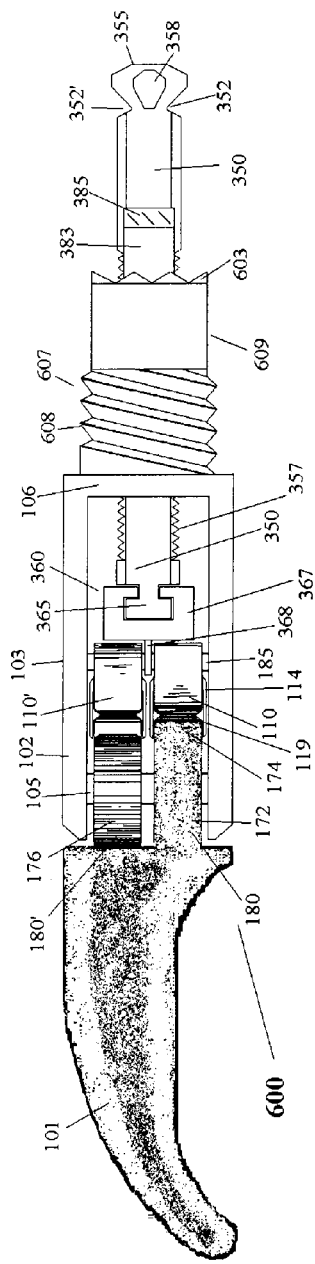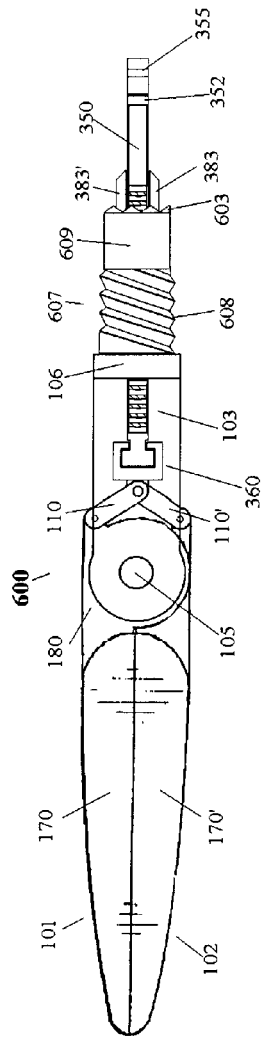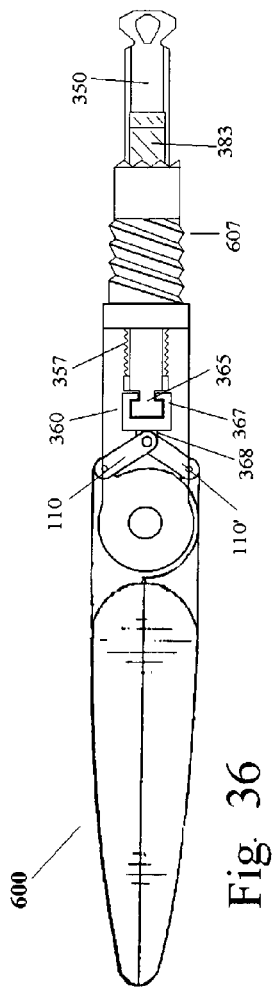
Fig. 34
Fig. 35
Fig. 36

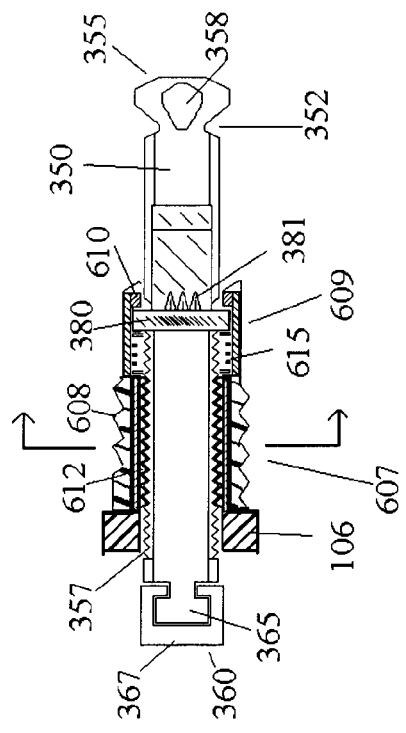
Fig. 37
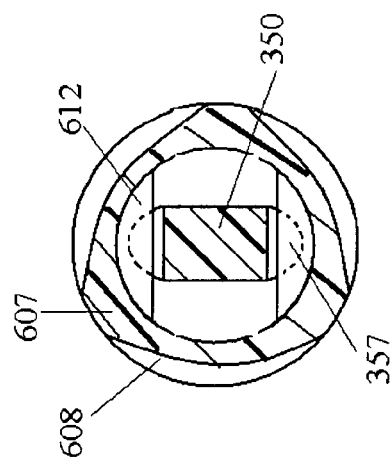
Fig. 38
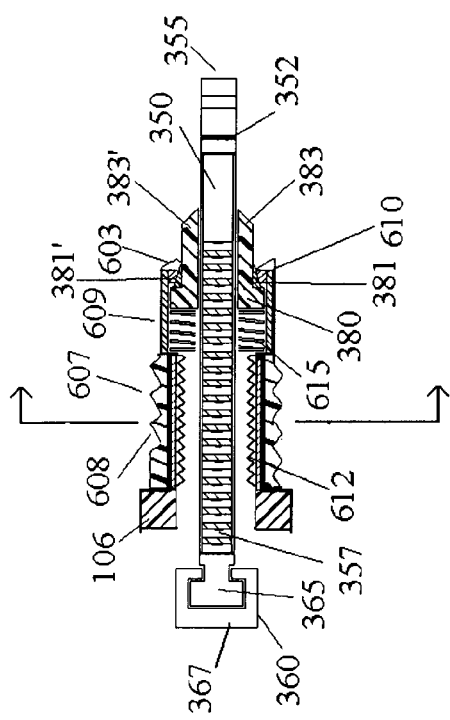
Fig. 39
Fig. 40

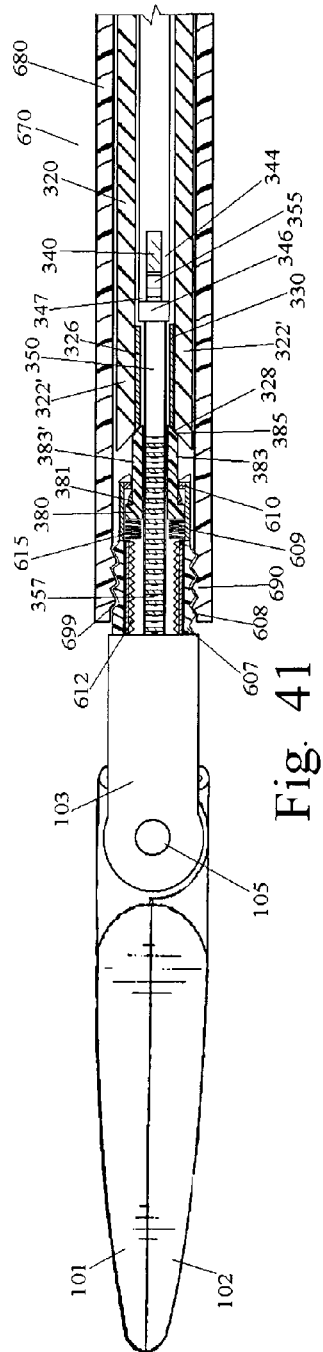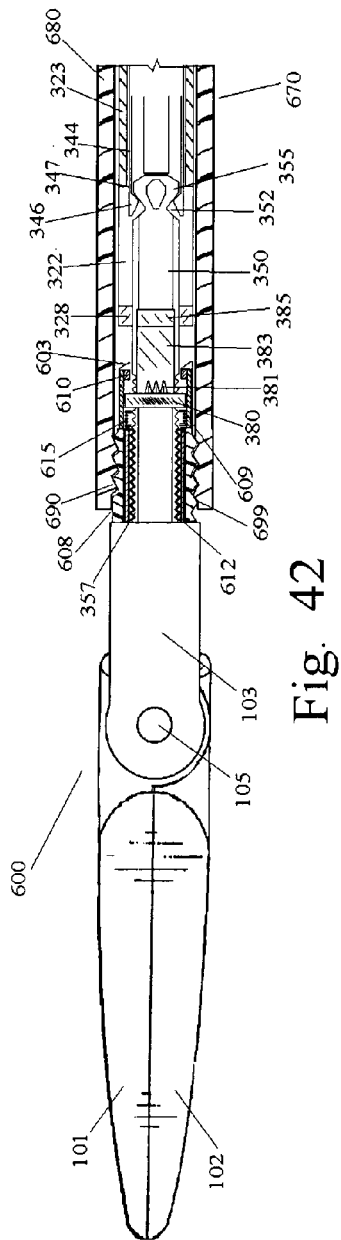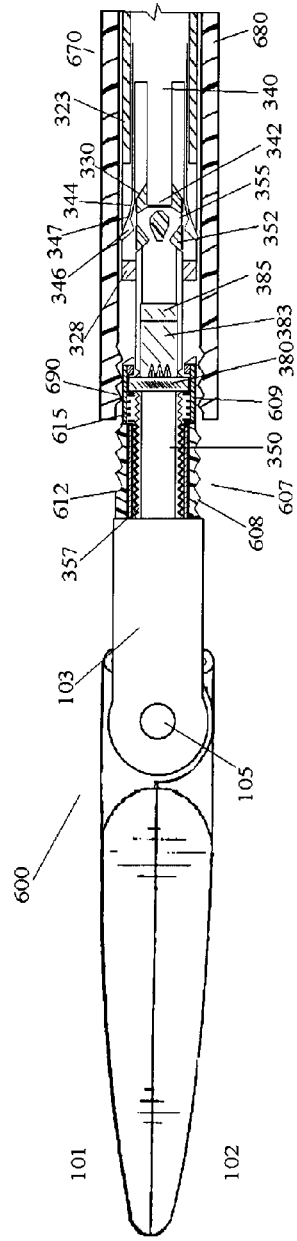

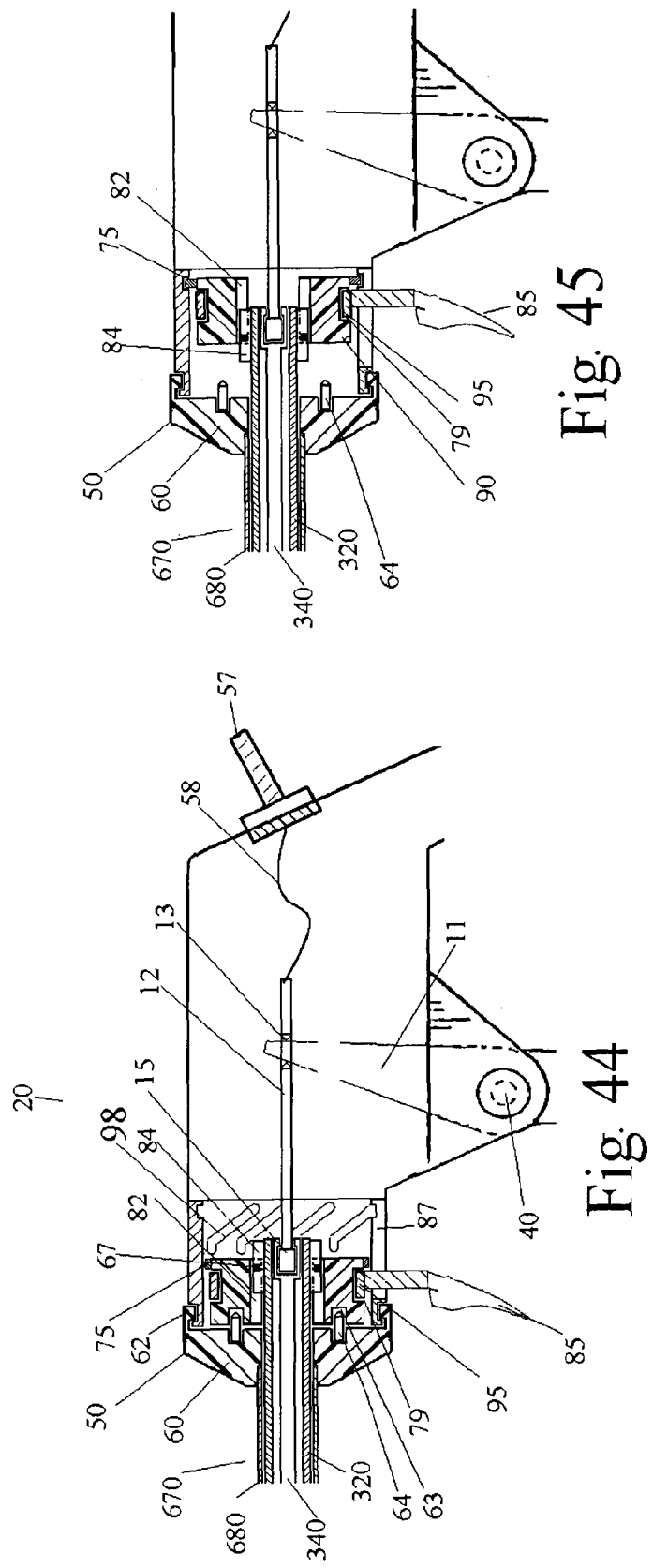

SURGICAL ENDOSCOPIC DEVICE WITH DETACHABLE END TOOL AS A CLAMP

The invention relates to an endoscopic surgical device with deployable clamp used in laparoscopic surgery, a clamp retrieving device and a method for their use.

In recent years, increasingly more surgeons replace the classic "open" surgery with endoscopic surgery techniques for accessing a surgical site in the abdominal and thoracic cavity, with endoscopic instruments that allow surgical approach through small access holes. The method requires the introduction of trocar (cannulas) in the abdominal or thoracic wall through small incisions. Through these trocars, with diameters between 5 and 12 mm, the devices needed for the intervention (laparoscope, electrocautery, special forceps, etc.) are inserted.

A haemostatic forceps is a pliers-like device which uses mechanical action between its jaws to compress blood vessels in order to stop a hemorrhage.

In open surgery, when the access to operating field is not limited, standard haemostatic forceps are used, which are applied directly on blood vessels or other bodily conducts, occluding them, thereafter the opening of forceps' jaws being blocked by means of a ratchet. In case of accidental damage to blood vessels, these forceps are applied, gathering between their jaws, the bleeding vessel, and surgery is continued after placing an underlying ligature. When tightening the ligature knot, the ratchet is released, followed by the opening of the forceps' jaws. These types of forceps can't be applied in endoscopic surgery because of the limits given by trocar size.

In endoscopic surgery, clamps are applied trough small access holes made by the surgeon. It is desirable to minimize the number of access holes for a certain intervention. Endoscopic clamps are either spring-tensioned, either applied using a threaded mechanism in order to occlude bodily conducts (segments of digestive tract, blood vessels).

During some endoscopic interventions, an accidental damage to blood vessels or of other bodily conducts may occur, lesions that would be difficult or impossible to repair endoscopically, resulting in the need of converting the endoscopic intervention to an "open surgery" intervention. Also, damage may occur in an anatomic segment which does not permit the primary application of monopolar or bipolar electrocauterization in order to achieve haemostasis because of nearby elements that may be thermally damaged. The application in haemostatic purpose of an ordinary laparoscopy forceps in order to provisionally solve a hemorrhage will inevitably lead to blocking the trocar in which it is inserted, thus limiting the number of tools that can remedy the lesion, or leading to the necessity of creating additional access routes.

There is, currently, a great variety of devices and methods adapted to endoscopic surgery aimed at achieving haemostasis, among which haemostasis clips, pre-tensioned clamps and thread operated clamps are mentioned.

Document EP1654992 describes a surgical system comprising a clamp, a delivery/retrieval device and an actuator. The delivery/retrieval device is removable connected to the surgical clamp and is used by the surgeon to either apply clamp, or to retrieve it from an anatomical site, it being driven by the actuator, the clamp being locked in a certain position of its jaws before and after it is applied at the anatomical site. The disadvantage of this technical solution is its intentional application, the technique not being feasible in case of accidental damage to blood vessels or other bodily conducts.

Document WO1998000066 describes a surgical clamp comprising a pair of jaws that can be maneuvered to occlude bodily conducts, namely of the digestive tract. Clamp applicator can be adapted to catch and maneuver the jaws from closed position to open and vice versa. Similar to the aforementioned patent, the disadvantage of this technical solution is its intentional application, the technique not being feasible in case of accidental damage to blood vessels or other bodily conducts.

Document U.S. Pat. No. 6,350,269 describes an applicator of surgical clips in order to occlude vascular segments, which is composed of a holder, a pair of applicators arms and a set of pending clips. The clip is pushed forward to be taken over by the arms and applied to the anatomical site, followed by the device to automatically reload. The disadvantage of this device and of all known clips applicators is the necessity of the vascular segment to be perfectly dissected and isolated to prevent dislodging of the clip, which makes it less feasible in case of accidental damage to vessels.

Document U.S. Pat. No. 5,368,600 presents an apparatus for the application of spring-loaded bulldog endoscopic clips comprising a handle, an elongated portion and a clip applicator. The disadvantage of this device is that the clamping force is the same regardless the thickness of the tissue caught by the clips' arms, which can lead to the dislocation of the clip.

Document U.S. Pat. No. 5,368,606 presents an endoscopic device consisting of a handle, an elongated shaft and a multitude of disposable tools that are screwed in the distal portion of the elongated shaft. This device acts as an ordinary laparoscopic forceps and the disadvantage is that assembling/disassembling of the disposable tool to the elongated shaft can be done only outside the human body.

The purpose of the invention is to achieve an endoscopic surgical instrument with its end tool detachable as a clamp, a clamp retrieving device and to provide a method for their use.

The problem the invention solves is the use of an endoscopic surgical instrument as a ordinary laparoscopic forceps, which, when accidental or deliberated damage to a blood vessel or other bodily conduct occurs, allows the detachment of its end tool at a site inside the body of the patient as a temporary occlusion clamp, in a similar manner to the hemostatic forceps used in open surgery, in order to facilitate the proper treatment of intraoperative injuries in areas where usual laparoscopic haemostasis methods would be hazardous or time consuming. After acquiring proper haemostasis by permanent methods with the aid of the said clamp, a clamp retrieving device is used to safely remove the clamp from the surgical site.

The endoscopic surgical instrument with deployable clamp eludes the disadvantages mentioned above in that it comprises a removable end tool detachably connected by a coupling device to an elongated shaft consisting of two concentric tubes, which can rotate about each other, in connection with a rotating assembly, that is fixed to a housing in which an push-pull rod, driven by a handle transmits the commands of the surgeon for the purposes of opening or closing the end tool's jaws, as well as the detachment/coupling of the end tool to the elongated shaft by operating the coupling device determined by the turning of the concentric tubes about each other, thus resulting in unscrewing/screwing of the end tool, and locking the jaws in their given position at the time it was detached.

The clamp retrieval device eliminates the disadvantages mentioned above in that it comprises a grasping element comprised of a fixed jaw with a distal hook and a mobile jaw, attached by an elongated shaft composed of concentric sheaths to a handle, which determines, by pressing a plunger, the sliding of some of some sheaths over the other(s) and the seizing of the clamp, the release of its jaws and the removal of the clamp from the human body.

The method of using the surgical instrument with detachable end tool as a clamp eliminates the disadvantages mentioned above in that it comprises the use of the instrument as a normal laparoscopic or thoracoscopic forceps during routine surgeries, and that in order to achieve hemostasis or occluding a bodily conduct, accidentally or intentionally sectioned during surgery, includes the grasping of the bodily conduct or blood vessel with clamp's jaws in order to achieve hemostasis, the detachment of the end tool as a temporary occlusion clamp inside the human body until the implementation of proper measures for hemostasis or definitive treatment of the lesion, followed by the removal of the clamp with an extraction device of the clamp, as well as replacing the end tool of the instrument with various forceps jaws and even scissors.

By applying the invention the following advantages are gained:

The possibility to use the instrument as a laparoscopic dissection or grasping forceps that can be also connected to electrical current, until the necessity arises, usually by intraoperative accident to deploy the end tool of the instrument consisting of its jaws together with a small frame as a temporary hemostatic/occlusion clamp;

The possibility to apply the clamp at an accidental bleeding site where the usual laparoscopic hemostasis methods could prove to be hazardous (dense adhesions or proximity of anatomical structures that could be damaged by thermal injury), followed by the proper treatment of the bleeding vessel by proper dissection and removal of the clamp in a safe manner.

The fact that the tip of the instrument is detachable, leads to the possibility of replacing it with various types of laparoscopic forceps jaws, including intestinal clamps and even scissors;

Also the detachment of the tip (of various types) could be deliberated in various endoscopic interventions;

The fact that the tip of the instrument is detachable, leads to the possibility of providing a reusable body of the device, while the tip could be of single use.

BRIEF DESCRIPTION OF THE DRAWINGS

FIG. 10 Perspective view of the clamp's locking system.

FIG. 11 Perspective view of a variant of the clamp's locking system

FIG. 12 Perspective view of a variant of the clamp's locking system

FIG. 13 Perspective view of another variant of the clamp's locking system

FIG. 14 Perspective view of another variant of the clamp's locking system

FIG. 16 Side view partially sectioned of clamp-elongated shaft coupling in one embodiment.

FIG. 17 Top view partially sectioned of the clamp-elongated shaft coupling in one embodiment FIG. 18 Side view in section of the clamp-elongated shaft coupling in one embodiment at the time of clamp detachment.

FIG. 24 Sectional side view of the handle, housing and rotating assembly.

FIG. 25 Sectional side view of the housing and rotating assembly.

FIG. 26 Top view of another embodiment of the clamp.

FIG. 27 Side view of another embodiment of the clamp.

FIG. 39 Side section view of clamp's framework in this embodiment.

FIG. 40 Cross-sectional view through the clamp's framework.

FIG. 41 Side view partially sectioned of clamp-elongated shaft coupling in this embodiment FIG. 42 Side view partially sectioned of clamp-elongated shaft coupling in this embodiment FIG. 43 Side view partially sectioned of clamp-elongated shaft coupling at the moment of clamp's detachment in this embodiment FIG. 44 Side-sectional view of the housing and rotating assembly in this embodiment.

FIG. 45 Side-sectional view of the housing and rotating assembly in this embodiment.

In the following description, I shall refer to as "proximal" the elements that are close to the surgeon, and as "distal" the elements located further away.

Figure 1:
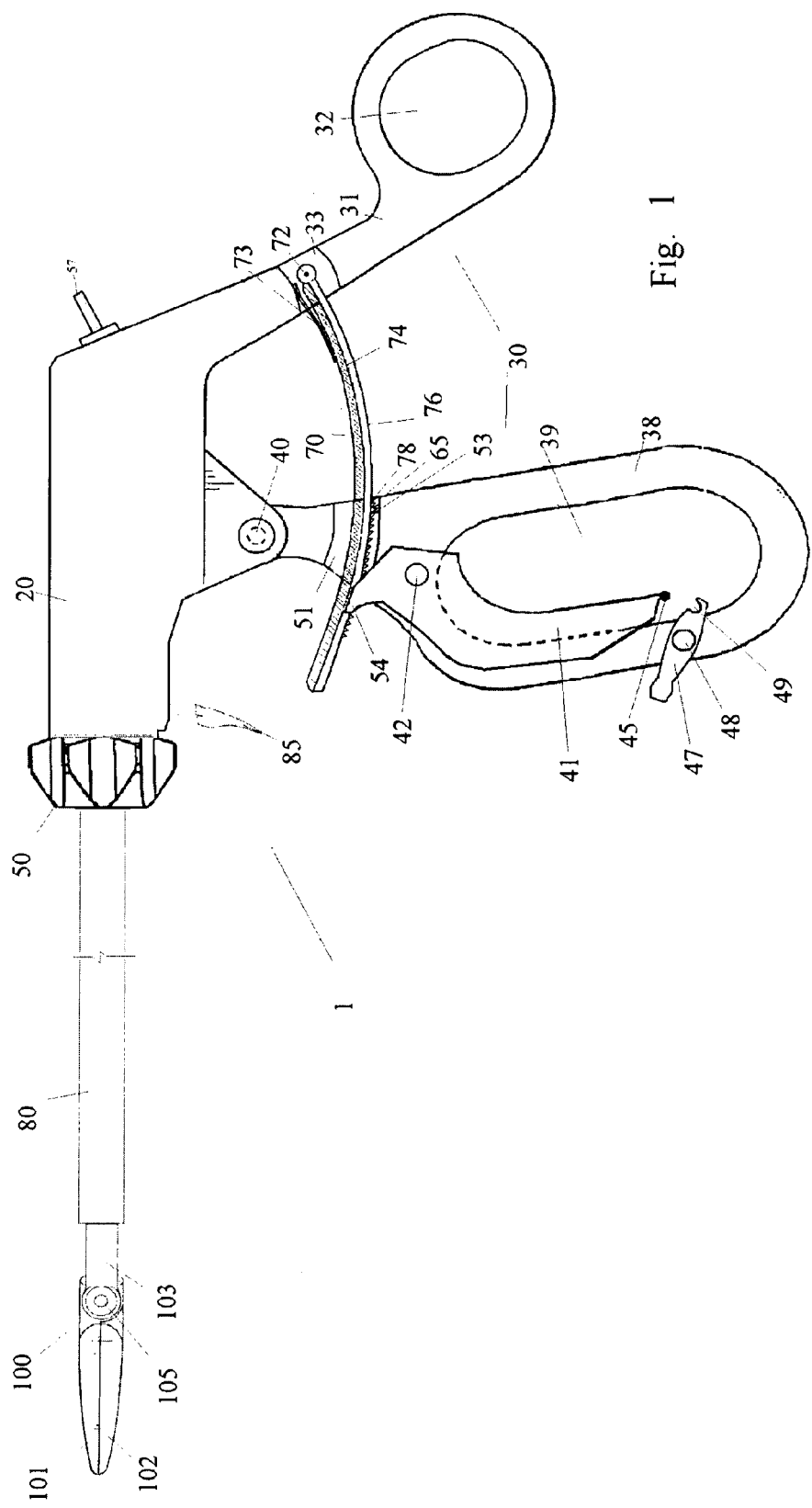
FIG. 1. Side view of an endoscopic surgical instrument with a detachable end tool.

FIG. 1 presents a side view of a embodiment of an endoscopic surgical instrument 1, endowed with the ability to detach the end tool as a haemostatic clamp during a surgical intervention, consisting of a handle 30, a housing 20, an elongated shaft 80, attached to the housing via a rotating assembly 50, and end tool 100, this presenting the forceps' jaws 101,102, mobile and opposable, which pivot around axle 105, that is attached to frame 103. At the level of the proximal side of housing 20, there is a metal rod 57 provided, intended for application at this level of a monopolar electrode for the including of the device in an electrical circuit.

Handle 30, located proximally, consists of an immobile arm 31 attached to housing 20 which has an orifice 32 through which the thumb of the surgeon is inserted, a recess 33, in which a pivot 72 is attached, on which rod 70 is attached.

Distal arm 38 of the handle has an orifice 39 designed to receive other fingers of the operator, and it is mobile, being articulated by pivot 40 to housing 20 of instrument 1. On the distal side of orifice 39, a flap mechanism 41 is shown, having a transversal rod 45 at its lower end, meant to be received, in need, in recess 49 of blocking element 47, which is manually operated at its distal end, pivoting around the axle 48. Also, mobile arm 38 of the handle has a recess 51 in its thickness, and at that level, on the lower surface, some indentations 53 are present, with the aim to engage with the indentations 78 located on the lower surface 76 of the rod 70, thus forming a ratchet mechanism 65. The flap 41 is attached to handle 38 by a pivot 42 and engages with rod 70 on its lower surface 74 through extension 54, which, if the flap is pushed, elevates the surface 76 of rod 70 that presents indentations 78, from indentations 53 of arm 38, permitting thus free movements of arm 38 of the handle 30. Rod 70 has an arciform shape and presents one inferior surface 74 which is plane, more elevated than the other inferior surface 76, at its level taking place the engagement with extension 54 of flap 41. Surface 76 located at a lower level presents in its distal portion indentations 78 which engage the indentations 53 of handle arm 38, thus forming a ratchet mechanism 65, thereby preventing the accidental opening of the handle arms 30. Also, rod 70 is held in place with teeth 78 and 53 engaged by the leaf spring 73 attached to the upper surface of recess 33 of the fixed arm 31.

The housing 20 of instrument 1 is mobile articulated with arm 38 of forceps handle by pin 40. Arm 31 of the handle is fixed to housing 20. In the distal portion of the housing, the rotating assembly 50 is attached. This presents outstanding knobs in order to facilitate the rotation of the elongated shaft 80 for a better approach in the operative field. In distal part of the housing 20, trigger assembly 85 is illustrated, whose extension enters the casing 20 through an inferior slot.

Elongated shaft 80 receives in its distal part the end tool 100 of the instrument, this presenting the jaws of the forceps 101,102, opposable, attached to frame 103 by axle 105.

Figure 2:
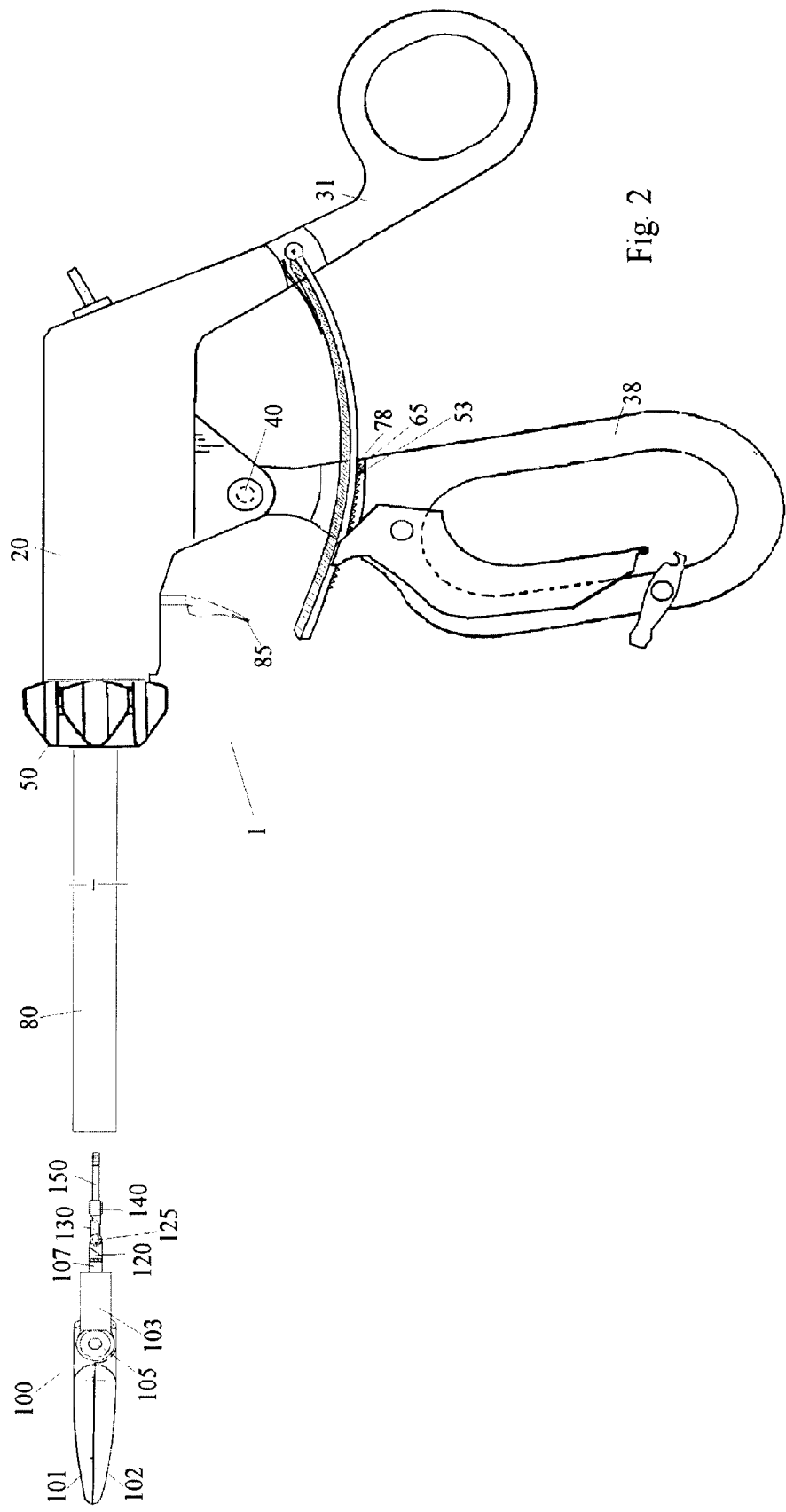
FIG. 2 Side view of an endoscopic surgical instrument with the end tool detached as a clamp.

FIG. 2 shows a side view of the embodiment of instrument 1 described above, with end tool 100 detached as a clamp from the level of the elongated shaft 80, for temporary clamping of a bleeding vessel or bodily conduct accidentally or intentionally injured intraoperative, until the measures for haemostasis or definitive treatment of the lesion are taken.

It can be observed that the mobile arm 38 of the handle is held in position by the engaging of teeth 53 and 78 of ratchet mechanism 65, and the trigger assembly 85 is pulled proximally by the surgeon. By inducing a rotational movement to the rotating assembly 50 with attending a quarter circle, clamp 100 is released, as will become obvious from subsequent description.

The clamp presents the forceps' jaws 101,102, opposable, attached to frame 103 by axle 105, around which they pivot. External frame 103, always located outside the elongated shaft 80, continues with the insertable frame 107, more narrow, which enters inside the elongated shaft 80, engaging with it by recesses 120. Also at the frame's 107 level, a blocking element 130 is attached, which overturns around axle 125. When released from the elongated shaft, the blocking fold is pushed in closed position, not allowing the push-pull rod 150, which mobilizes the clamp's jaws, to perform translational motion, thus maintaining the clamp's opposable jaws 101,102 fixed. Unlocking element 140 is represented by a wedge centered by push-pull rod 150, which, when it is pushed distally, elevates blocking element 130 from the closed position, permitting thus the mobilization of push-pull rod 150.

Figure 3:
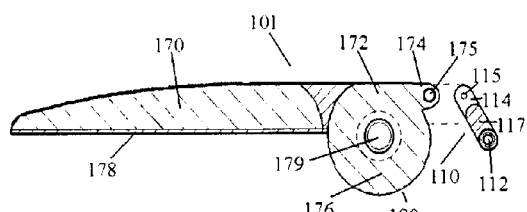
FIG. 3 Side view, partially sectioned through the clamp's upper jaw.

FIG. 3 shows a side section view through the superior jaw 101 of clamp 100, this presenting a gripping part 170, with a lower surface 178, provided with teeth that do not allow to the tissue caught between forceps jaws to side-slip, and a cylindrical part 180, which fits between the frame's 103 arms.

Jaw's segment 170 gradually increases in thickness towards the proximal, where it joins the cylindrical segment 180 of jaw 101, which pivots around the axle inserted into central orifice 179. The cylindrical segment has an upper part 172, located in the extension of the forceps jaw and an inferior one 176. At the level of portion 172, towards proximal a protuberance 174 with an orifice 175 is found, which receives the axle 115 of the lever 110. This lever is made of a solid portion 117, and two lateral blades 114 in its continuation, which bilaterally address the protuberance 174 of cylindrical segment 180, articulating with it by pivot 115. It is preferably that the contact surface 119 between solid portion 117 of lever 110 and protuberance 174 to be indented or rough for their better gearing and a more efficient transmission of force. At the proximal end, the lever has an orifice 112.

Figure 4:
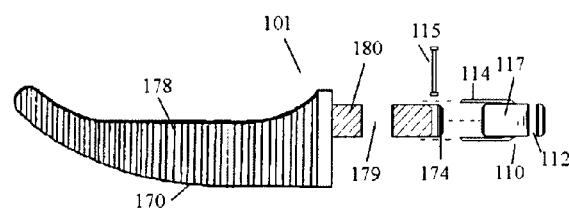
FIG. 4 Bottom view of the clamp's upper jaw.

FIG. 4 shows an inferior view of the clamp's upper jaw 101, composed of a portion with prehensile function 170, having a concave and a convex edge, a gripping surface provided with teeth 178, and a cylindrical segment 180, featured in cross-section that pivots around the orifice 179. The protuberance 174 can be also seen, located the articulation with lever 110 is made by axle 115 which attaches the blades 114 to protuberance 174, and through direct contact between protuberance 174 and solid portion 117 of lever 110. At the proximal end, the lever 110 has an orifice 112.

Figure 5:
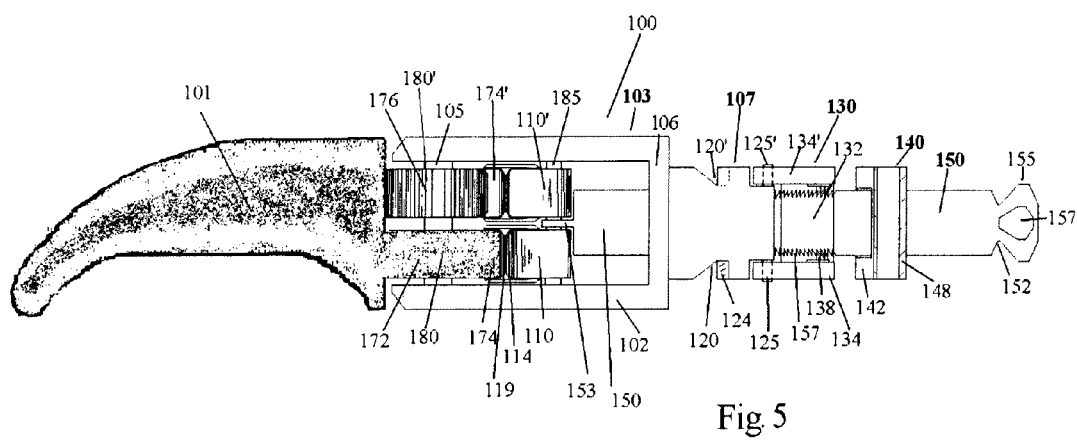
FIG. 5 Top view of one embodiment of the clamp.

FIG. 5 shows a top view of a this embodiment of the clamp 100, viewing the upper jaw 101, which continues proximally to its cylindrical segment 180, viewing the top surface 172 of it, and which is articulated at its prominence 174 with the lever 110. Parallel to the cylindrical segment 180 is seen the inferior portion 176' of cylindrical segment of the opposite forceps jaw and prominence 174', articulating the lever 110' in a similar manner. Note the external frame 103 comprising two parallel arms 102, which include cylindrical segments 180 and 180' of the forceps' jaws, in their center being routed by pivot 105, that is fixed on the frame 103, around which they overturn, being driven by levers 110, 110'. Levers rotate with their proximal part around the axis 185, which runs in a longitudinal recess 117 located on the inner surface of the frame 103 and are anchored on the distal end 153 of push-pull rod 150. The rod is centrally crossing the transverse part 106 of the frame 103. In the distal part, push-pull rod 150 presents a narrowing 153, which is interposed between the levers 110, 110', hereby anchoring the pivot 185. The wider terminal portion of push-pull rod 150 also serves to push the lever 110 towards the distal increasing thus the force which will be transmitted for closing the forceps' jaws.

Figure 15:
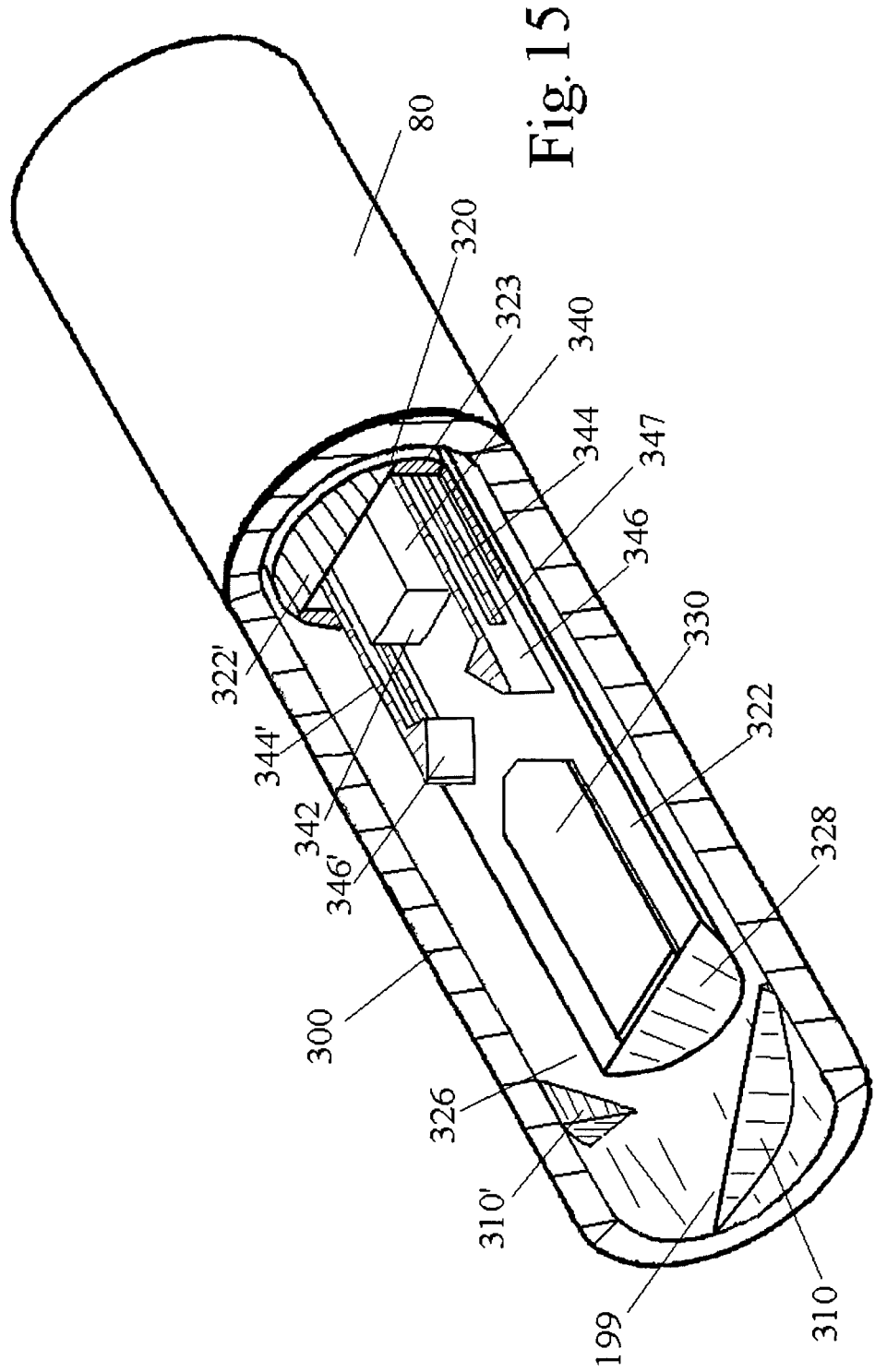
FIG. 15 Sectional perspective view of the elongated shaft's distal end.

Continuing, to the proximal, is the insertable frame 107, which is attached to the transverse part 106 of external frame 103, being narrower than it, and showing in the middle of the lateral sides a thread composed of two lateral sockets, 120, 120' of triangular form, with a distal vertical surface 122, and a proximal oblique one 124, the two oblique surfaces 124 being oriented in opposite directions in order to be screwed in the distal part of the elongated shaft 80 (FIG. 15).

The proximal part of frame 107 presents a narrowing from which two axles 125, 125' derive, around which the blocking flap 130 pivots. The blocking flap presents three surfaces that partially circumscribe the push-pull rod 150, a superior one 132 which is illustrated here transparent and two side surfaces 134, provided with indentations 138 on the inside, designed to engage with teeth 157 of push-pull rod 150, thus achieving the blocking of its movements. Continued toward proximal, also centered by push-pull rod 150, which it circumscribes is unblocking element 140. It presents to the distal two side surfaces 142, shaped as a wedge with an oblique upper surface, which when unblocking element 140 is pushed toward the distal, disengage indentations 138 of the blocking flap 130 from the teeth 157 of push-pull rod 150, thus unlocking it and allowing its free translational movement. Also, unlocking element 140 presents in its proximal part a multiangulated surface 148.

The push-pull rod 150 has in its proximal part two triangular sockets 152, bordering a polygonal segment 155, the acting on push-pull rod 150 being made at this level, as will result in further description. Segment 155 of push-pull rod 150 presents centrally an orifice 157.

Figure 6:
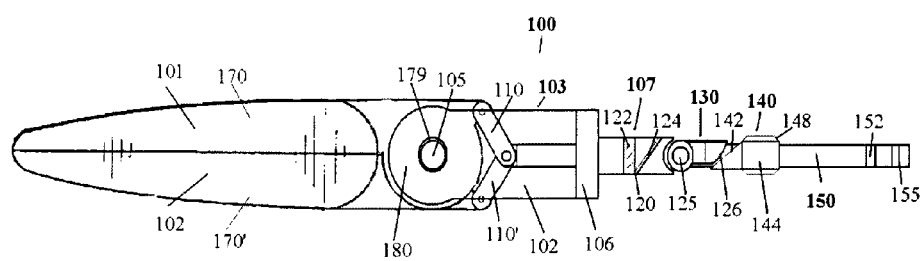
FIG. 6 Side view of one embodiment of the clamp.

FIG. 6 shows a side view of clamp 100. Forceps' jaws 101,102 present a portion with prehensional purpose 170, 170', continuing with their correspondent cylindrical segment 180. At the level of orifice 179 of the cylindrical segment, it is attached to frame 103, figured here transparently, by pivot axle 105, which allows the forceps jaws to swing, they being trained by levers 110,110', which are in turn mobilized by push-pull rod 150, which is pushed or withdrawn by its proximal segment 155 and traverses centrally from proximal to the distal unblocking element 140, blocking flap 130, frame 107, transverse portion 106 of external frame 103. The rod leads in case of its pushing towards the distal the closing of forceps' jaws and in case of its pulling towards the proximal their opening by transmitting the force along the levers 110.

The frame 103 presents of two paralleled arms 102, which include the cylindrical segments 180 of the forceps jaws. In the distal portion of frame 103, axle 105 is attached, around which the forceps' jaws 101,102 pivot. In the proximal portion, the frame 103 presents a transverse part centrally crossed by push-pull rod 150.

The external frame 103 is always located outside the elongated shaft and its transverse portion 106 continues with insertable frame 107, of parallelepiped shape in this embodiment, which presents in its proximal portion a narrowing on which an axle 125 is assembled, around which blocking fold 130 pivots. In the middle portion of the frame 107 on its lateral sides are two sockets 120 located diametrically opposite, which form together a thread, for anchoring the clamp 100 to the elongated shaft 80 as will become obvious from further description. These recesses have a distal vertical surface 122, and a proximal obliquely oriented surface 124, in order to be screwed into the external sheath 300 of elongated shaft 80.

The blocking flap 130 pivots around axle 125, which is attached to frame 107, presenting three surfaces that partially comprise the push-pull rod 150. In the position of flap 130 shown in the drawing, it blocks the free movement of the push-pull rod 150. The lateral surfaces of the flap present in their proximal side a curved edge 126. This has the purpose to be engaged by wedge 142 of unlocking element 140, in order to elevate flap 130, respectively to unlock push-pull rod 150.

Unlocking element 140 presents a proximal polygonal area 144, which circumscribes push-pull rod 150 and a distal triangular area 142, placed sideways to the rod. It aims to catch on, when unlocking element 140 is pushed toward the distal, the blocking flap 130, at its proximal edge 126 of the lateral surface, thus forcing it to swing around the axle 125 and to release push-pull rod 150. Unlocking element 140 presents in its proximal part the angulated surface 148.

The push-pull rod 150 has in its proximal portion, the segment 155, bordered by two lateral symmetrical sockets 152.

Figure 7:
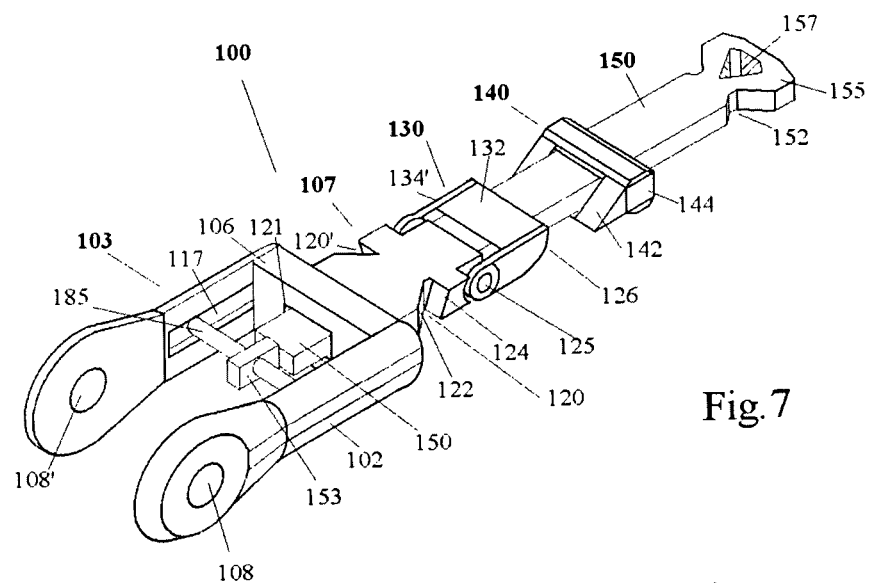
FIG. 7 Perspective view of an embodiment of the clamp.

FIG. 7 shows a perspective view of a preferable embodiment of the clamp, making abstraction of forceps arms and the axis around they pivot.

Frame 103 is illustrated with its parallel arms 102, which present in their distal portion an orifice 108, 108, meant to receive axle 105 (FIG. 5), around which the forceps' jaws pivot 101,102 (FIG. 5). Also side arms 102 of external frame presents on their internal surface a recess 117, in which axle 185 glides, this being attached to the distal terminal portion 153 of push-pull rod 150, which crosses the transversal portion 106 of frame 103 through a central quadrangular orifice 121. The frame 107, narrower than frame 103 which it continues to the proximal, has the purpose to anchor clamp 100 to external sheath 300 of the elongated shaft 80 (FIG. 15). Insertable frame 107 is of quadrangle shape on transversal section, being centrally crossed by push-pull rod 150. The frame presents on its lateral sides two triangular recesses 120,120' forming a screw. The frame 107 narrows proximally, presenting at this level two axles 125 oppositely located, around which blocking flap 130 pivots. In this image, the flap is in "closed" position, blocking the free movement of push-pull rod 150. The flap 130 consists of an horizontal surface 132, superiorly located, which unites the two lateral surfaces 134, 134', which in their proximal part present a curved edge 126.

Continuing to proximal, and figurated distant of blocking flap 130, is unblocking element 140 centered by push-pull rod 150, having a polygonal portion 144, which continues sideways to the rod with wedge 142, having the purpose to elevate flap 130 off the push-pull rod 150.

The proximal portion of push-pull rod 150 presents two triangular recesses 152 which border a segment 155 with orifice 157.

Figure 8:
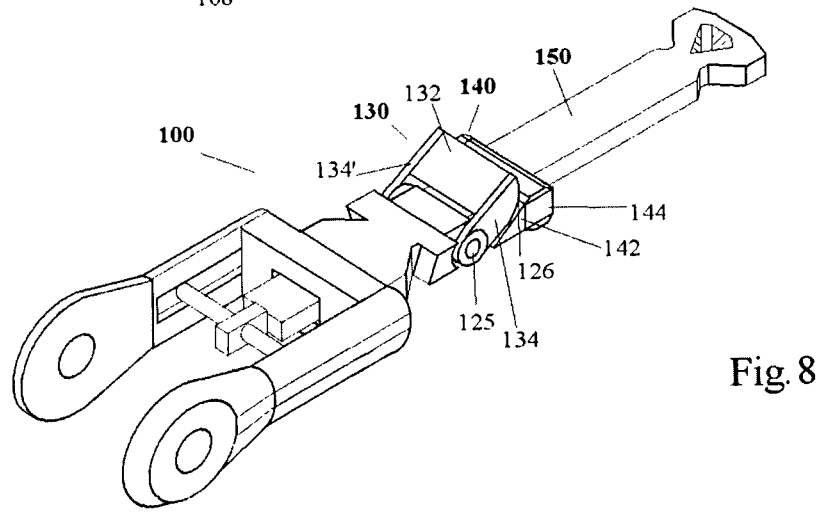
FIG. 8 Perspective view of an embodiment of the clamp.

FIG. 8 presents a perspective view of clamp 100 of the version illustrated in previous figure, having the same elements, except for unlocking element 140 which is pushed distally along push-pull rod 150, catching with its wedge part 142 the curved edge 126 of side surface 134 of blocking flap 130, urging it to an overturning movement around axle 125, realizing thus its elevation from the plan of push-pull rod 150, unlocking it and permitting its translational free movement.

Figure 9:
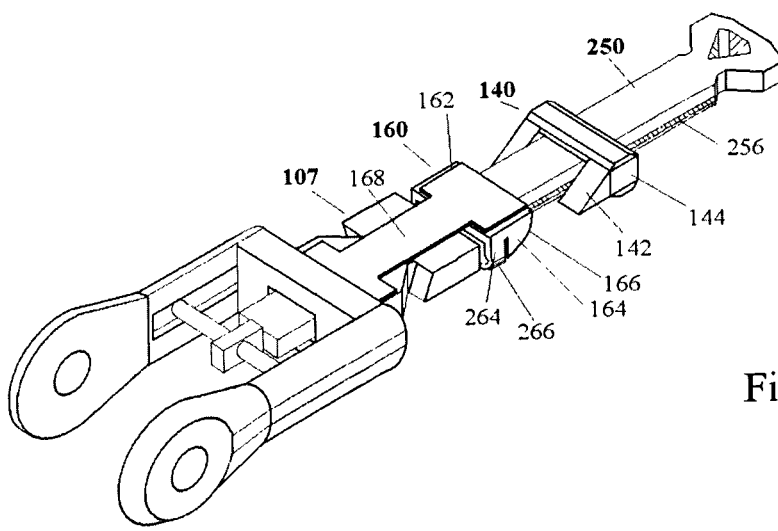
FIG. 9 Perspective view of another embodiment of the clamp.

FIG. 9 shows a perspective view of another embodiment of clamp 100, with the difference from the version presented in FIGS. 7 and 8 that the attachment of the locking flap 160 of the frame 107, is not by an axle located at the proximal end of the insertable framework, but through an upper leaf plate 168, that is attached to frame 107 in its distal portion, thus allowing the free movement of plate 168, respectively the elevation of the locking flap 160 off the push-pull rod 250. Note that the push-pull rod 250 presents along the lateral sides an edge 256.

The blocking flap 160 consists of an upper surface 162, attached to leaf plate 168, which connects the two side surfaces 164. Lateral surfaces show a proximal rigid portion 164 with a proximal curved edge 166, meant to be engaged on by the wedged portion 142 of the unlocking element 140 when pushed towards the distal, thus elevating flap 160 of the push-pull rod 250, allowing free translational movement of it. On the distal side of the lateral surfaces, separated from the rigid segment 164, there is a flexible segment 264, with a lower bent termination 266, providing a clamp mechanism around the edge 256 of the push-pull rod 250 when flap 160 is in the closed position in order to maintain a solid grip.

The proximal part of the push-pull rod 250 has the same elements as those described in previous figures, and lower proximal portion of the frame 107 is designed to prevent excessive movement of the unlocking element 140 towards distally.

The frame 103 has the same elements as in the previous figures and the sockets 120,120' that compose a thread from the frame 107 are having the same specifications as those described above.

FIG. 10 shows a perspective view of the clamp's rod blocking system, composed of the frame 107, which shows a thread composed of two lateral sockets 120 and 120', and a narrowing in its proximal portion where two axles 125,125' are anchored, around them the blocking flap 130 is pivoting, in this image it being shown in a opened position, disposed away from its place of action.

The blocking flap has three surfaces which partially circumscribe push-pull rod 150, namely a horizontal top surface 132 which connects two vertical surfaces 134. Vertical surfaces present in their distal portion, two holes 135,135' for the engagement with the pivots 125,125', and a proximal bent edge 126, 126' which is held elevated by the contact with the distal portion 142 of the unlocking element 140, pushed towards the distal.

On the inner side of the vertical surface 134 of the locking flap 130, there is a batch of teeth 138, which, in the moment when the flap 130 is pushed in the "closed" position, engages with lateral indentations 157 of the push-pull rod 150, blocking thus its free translational movement. Also, the unlocking element 140 is pushed toward the proximal when applying the blocking flap 130 on the push-pull rod 150.

FIG. 11 presents another embodiment of the locking element, consisting of the frame 107 with the two lateral sockets 120, 120' and axles 125, 125' described above, the frame being centrally transversed by the push-pull rod 250.

Locking flap 230, which is disposed in the figure in open position, is composed from a horizontal surface 232, which shows in its distal side two rings which border the orifices 235, 235' which pivot around the axles 125, 125' of the frame 107.

At the middle of the lower surface of the horizontal surface 232, in its proximal portion there is a cross slide 238 together with a supporting element 239. In case of inwards tipping of the locking fold 230, the slide 238 will enter into the transverse sockets 257, cut in the median portion of the push-pull rod 250.

The lateral surfaces of the fold are consisted of a rigid proximal portion 234, with a proximal curved edge 236, which will be elevated together with the fold, by driving towards the distal the unlocking element 140, through its wedged portion 142, as previously described.

Inside the distal portion of lateral surface, separated from the rigid surface 234, there is a flexible segment 264 with bent lower edge 266, acting as a clamp which maintains the locking fold 230 in a closed position by sliding over the edge 256 of the push-pull rod 250, the distance between the two edges of the rod being greater than the distance between the peaks of the curved edges 266, 266'.

FIG. 12 presents a perspective inferior lateral view of embodiment shown in FIG. 11, with flap 230 in closed position. The frame 107 is represented, as previously described, with the two lateral axles 125, around which the locking fold 230 is swinging, engaging the push-pull rod 250, thus blocking its translation movement.

Note the locking fold's 230 lateral surface consisting of a rigid proximal portion with a proximal curved edge 234, drawn away from wedged portion 142 of the unlocking element 140, and elastic segment 264, presenting a lower curve 266, which circumscribes the edge 256 of the push-pull rod 250, blocking a too easy opening of the locking fold 230.

FIG. 13 presents an inferior-lateral perspective view of the locking fold 160, as previously described in FIG. 9. It consists of the frame 107 which presents a thread composed of two lateral sockets 120, 120' meant to anchor the end tool to the elongated shaft.

The engagement between the frame 107 and locking fold is performed through a elastic metal plate 168, which is attached on the distal top of the frame 107, the locking element 160 being shown in opened position, distantly to the frame, namely from the push-pull rod 250.

Proximal, the metal plate 168 is attached to the upper transverse surface 162 of the blocking fold. Its construction is similar to the fold version introduced in FIG. 11, except for the engagement manner with the frame 107.

In the middle of the horizontal upper surface 162, on its lower surface, is a proximally located transverse lamella 238, together with a longitudinal supporting element 239, which penetrates, in case of downward placement of fold 160, one of the transversal sockets 257 of push-pull rod 250, thus stopping the translational movement of push-pull rod 250.

Lateral surfaces present a rigid portion 164, with a proximal curved edge 166, serving for the elevation of the fold 160 from the push-pull rod 250, thereby unlocking it, when engaged by the wedged portion 142 of the unlocking element 140.

At the lateral distal portion of the fold 160 there is an elastic segment 264 with a curved lower edge 266, acting as a clamp to maintain the locking fold 160 closed through the mechanism described above.

FIG. 14 presents an inferior lateral perspective view of clamp's locking system, in the version described in FIG. 13, with the flap in the "closed" position. It presents the frame 107 with the two sockets 120, 120' described above, the unlocking element 140 located at a distance from locking fold 160 this being applied to the upper horizontal surface on push-pull rod 250, thereby blocking its movement.

Note on the lateral surface of the fold, a proximal rigid part 164, showing a proximal curved edge 166, and a flexible distal segment 264 with its lower curved edge 266, that includes as a clamp the edge 256 of the push-pull rod 250. In this case accidental free movements are not allowed of locking fold 160 unless the application of a sufficient strength by unlocking element 140 on the proximal edge 166.

FIG. 15 presents a sectional elevation view of the terminal part of the elongated shaft 80. Elongated shaft consists of two concentric tubes, an external tube 300, circular on the transverse section, circumscribing the internal tube 320 centrally routed by a drive rod 340, whose translational movement along the longitudinal axis of the elongated shaft leads to the opening/closing the jaws of the clamp.

Between the external tube 300 and internal one 320 there is a cleavage space, they not being fused together, the external tube having in relation with the internal one, the possibility of circular movements which will lead to attaching/detaching the clamp by screwing/unscrewing. In its distal portion, the external tube 300 shows inwards a fastening mechanism of the clamp 199, consisting of two lamellas—a lower and an upper one 310, 310', which are visualized partially cut, rigid, obliquely oriented in relation with the tube's axis, on section of triangular shape, the thickness decreasing progressively from the center to the lamella lateral borders, to mention the fact that the internal edge of the lamella is straight and the insertion base is thicker.

These lamellas, which are meant to be inserted into sockets 120, 120' of the insertable frame of the clamp (FIG. 7), described above, delimit a quadrilateral slot at the distal orifice of the elongated shaft, with its long axis oriented vertically when the clamp is engaged to the elongated shaft, and horizontally, by rotating the external tube around the internal one, as shown in the figure when the clamp is in the process of detachment or attachment.

The alignment of the lamellas 310, 310', is oblique and in opposite direction so in the rotational motion of the external tube 300 in relation with the internal one 320, will result a motion of screwing/unscrewing of the clamp, depending on the direction of rotation, of a quarter circle. Also, their oblique orientation increases the stability of the clamp in the coupling with the elongated shaft.

The drive rod 340 centrally routes the elongated shaft 80 respectively the internal tube 320, presenting in its distal portion a terminal quadrilateral surface 342, which is to be applied on the proximal portion 155 of the clamp rod, pushing it toward distally.

Also, in the distal part of the rod 340 there is the clamp rod fastening mechanism 347, consisting of two symmetric elastic lamellas 344, 344' located laterally from terminal surface 342, applied on the opposite lateral sides of the drive rod 340, presenting in their distal part two triangular thickenings 346, 346', which are designed to be inserted into recesses 152 that border the distal side of the clamp rod 155 having the purpose to pull toward proximal the clamp push-pull rod 150 together with the drive rod 340.

The distal portion of the internal tube 320 ends in two parallel arms 322 inwardly flattened, each with transversal section of circular segment, the upper arm 322' being cut in this figure. On the internal surface of the arms 322, medially, there is a prominent surface 330 having the width lower than that of the arms.

The arms 322 delimit a quadrilateral slot 326, with its long axis horizontally oriented, at its level being made the engagement between the proximal portion of the clamp's push-pull rod 150 and the drive rod 340. The arm 322 ends distally in an oblique surface 328, which firstly aims to facilitate the insertion of the clamp in the elongated shaft by directing the clamp's rod toward the slot 326, which has a corresponding thickness, and on the other side, the oblique surfaces have the same slope as the proximal oblique cut edges 148 (FIG. 6) of the unlocking element 140.

The prominent surface 330, ends distally in the oblique surface 328 and proximally presents the trapezoidal edge which catches on the triangular elements 346, 346' of the fastening mechanism of clamp rod 347, when it is pushed towards the distal for the deployment of the clamp.

Regarding to the slot 326 delimited by the two terminal arms 322 of the internal tube 320, it has a lower width in the prominent portion of the surfaces 330, sufficient to receive the rod of the clamp with its short transverse diameter, but the width of the slot is shorter than elements 346 width, forcing them through the trapezoidal proximal surface edge 330 to part from the midline, disengaging thus from the sockets 152 of the clamp rod in which they are anchored.

In a more proximal plan than the prominent surface 330, at the terminal side of the internal tube 320 two blades 323, are added which connect the two arms 322, resulting in an outer circular section that forms the internal tube's body 320 and to the inside a quadrilateral empty section, routed by the drive rod 340.

Thus, depending on the position of drive rod 340, will result, either the disengaging of the triangular elements 346 from the proximal sockets of the clamp rod by the surface 330 which pushes them sideways, when drive rod 340 is pushed toward the distal end of the tube 320 for clamp deployment, or either their engagement, when drive rod 340 is withdrawn toward proximal due to pushing elements 346 towards medial by the blades 323, as happens while the clamp is attached to the elongated shaft 80.

Also, the rod is withdrawn inside the tube 320 between blades 323 during the use as a laparoscopic forceps of the endoscopic instrument 1, preventing the accidental detachment of the clamp rod from the element 346 of the drive rod 340.

FIG. 16 presents a sectional side-view in of the clamp-elongated shaft coupling in an embodiment.

Clamp 100, as previously described, presents the forceps jaws 101, 102', which are continued with the cylindrical segment 180, pivoting around axis 105, which is fixed on the frame 103 (which is transparently shown).

Forceps jaws' movement is transmitted through levers 110, 110', those being mobilized by pushing/pulling the push-pull rod 150, which crosses centrally the transverse portion 106 of external frame 103, the insertable frame 107, the locking fold 130 and the unlocking element 140, all these elements being described above.

Elongated shaft 80 comprises an external tube 300 which circumscribes the internal tube 320 and surpasses it distally, the internal tube being shorter than the external one. At the distal portion of the external tube 300, it presents inwards a fastening mechanism 199 consisted of two lamellas 310, located diametrically opposite, obliquely sloped towards the axis of the elongated shaft, which, by rotating the external tube 300 in relation to the internal one 320, are screwed into sockets 120, located on lateral sides of the insertable frame 107 of clamp 100, these being equally sloped on their proximal surface 124 as the lamellas 310.

The engaging of the lamella 310 and socket 120 is solid when lamella 310 is presented to it with its thickest portion (the middle), meaning after the external tube's rotation at 90° in relation with the internal one, knowing that the internal edge of the lamella is straight.

The unlocking element 140 is pushed distally when inserting the clamp 100 inside the elongated shaft 80 and the lamella 310 of the external tube 300 is screwed into clamp's socket 120. Thus, the unlocking element elevates the locking fold 130 from push-pull rod 150 by its wedged portion 142, which engages the edge 126 of the flap 130, making it pivot around axis 125. Thus, the free movements of translation of the push-pull rod 150 are allowed, so are the movements of the forceps jaws 101, 102 while the fold 130 is elevated.

Drive rod 340 routes centrally the internal tube 320, to it being attached the clamp rod fastening mechanism 347, consisted of lamella 344 which distally ends in triangular element 346, that catches the proximal portion 155 of the push-pull rod 150 at recesses 152.

When pushing the drive rod 340 toward distal, this will transmit the force toward push-pull rod 150 of the clamp, and by pulling, the force will be transmitted through lamellas 344, respectively to the triangular element 346, which do not allow the slippage of the proximal portion 155 of push-pull rod 150.

Internal tube 320 ends distally in two parallel arms 322, 322', which internally show a prominent proximal surface 330, bordering together a polygonal slot 326 sufficient to permit the introduction of push-pull rod 150.

FIG. 17 presents a sectional top view of the clamp-elongated shaft's coupling in this embodiment.

Clamp 100 presents the upper forceps jaw 101, which continues with its according cylindrical segment 180. Parallel to it and centered on the pivot 105 of the external frame there the cylindrical segment 180' of the lower forceps jaw.

Cylindrical segments are engaged by the levers 110, 110' in the manner described above, these, being trained by the push-pull rod 150.

Elongated shaft consists of an external tube 300, which is rotated by 90 degrees in relation to the internal tube 320, thus, making the fastening mechanism of the clamp 199, comprising lamellas 310, 310' to be inserted and screwed into sockets 120, 120' of the insertable frame 107 of the clamp, thus, locking it in the distal portion of the elongated shaft 80.

By screwing, the translation toward proximal of clamp 100 is made, fixing the unlocking element 140 through its proximal oblique surface 148, to the terminal oblique surfaces 328 of the internal sheath's 320 arms 322,322'.

At the distal side of tube 320, an inner quadrilateral slot is delimited, in which the rods 340 and 150 engage.

With the clamp 100 engaged to the elongated shaft 80 by lamellas 310 of the external tube screwed into sockets 120, 120' of the insertable frame 107, the drive rod 340 together with lamellas 344 and elements 346 will remain within the internal tube, bordered by lateral blades 323, which do not allow the elements 346 to side away from the midline, so do not allow their disengaging from sockets 152 that border the proximal portion 155 of the push-pull rod 150.

Figure 18:
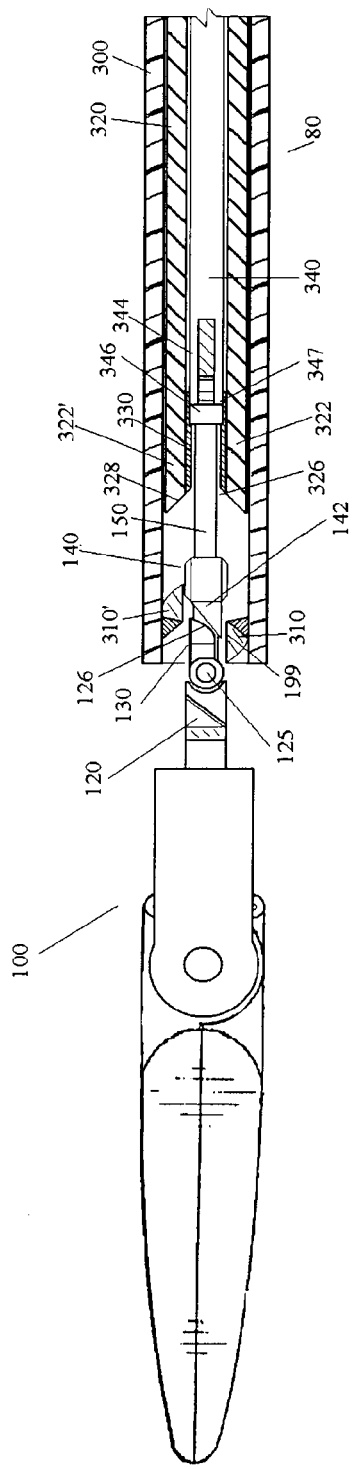
Figure 19:
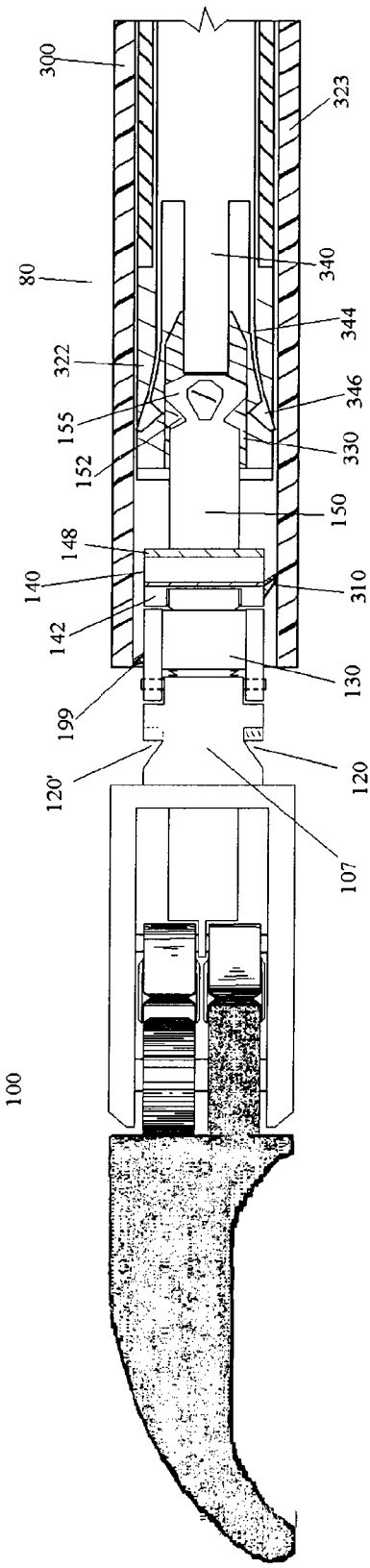
FIG. 19 Top view in section of the clamp-elongated shaft coupling in one embodiment at the time of clamp detachment.

FIGS. 18 and 19 presents a sectional lateral side view, respectively upper view of the coupling between clamp-elongated shaft at the time of attaching-detaching the clamp.

Clamp 100, having the structural elements described above is presented for insertion into the elongated shaft 80 (described above) with blocking flap 130 applied on the push-pull rod 150, thus blocking its movement. This allows the clamp push-pull rod 150 to fully enter into the slot 326, which is delimited by terminal arms 322, 322' of the internal tube 320.

Note that the external tube 300 is not rotated relative to the internal 320, so that the slot delimited by the two transverse oblique lamellas 310, 310' with triangular section and opposite orientation, has the same orientation as slot 326 delimited by the two terminal arms 322, 322' of the internal tube, so that the introduction of the push-pull rod 150, the unlocking element 140, the locking fold 130 in the closed position and the insertable frame 107 is allowed.

When the unlocking element 140 is applied to the surface 328 of the terminal arms 322,322' of the internal tube 320, with the screwing of the lamellas 310, 310' of external tube into sockets 120, 120' of the insertable frame 107, this meaning the turning of a quarter circle of the external tube relative to the internal one, the unlocking element 140 will be pushed towards distal, and approaches through its wedged surface 142 the curved edge 126 of lateral surfaces of the locking fold 130.

The fold 130 is then elevated from the push-pull rod 150, unlocking it, resulting the configuration model of the instrument presented in FIG. 16 having the slot delimited by lamellas 310, 310' of external tube 300 perpendicularly oriented to slot 326.

Drive rod 340 is engaging the proximal portion of push-pull rod 150 with its distal surface 342 and the fastening mechanism of the clamp's rod 347, comprising of the elements 346, attached to drive rod 340 through lamellas 344, being shown apart from the midline, being directed this way by prominent surface 330, having its proximal edge of trapezoidal shape.

As the clamp push-pull rod 150 enters in the slot 326 of the internal tube, it pushes toward the proximal the drive rod 340, bringing the elements 346 of the rod along with it, progressively releasing them from the edges of the prominent surfaces, thus allowing them to close toward median until engaging with sockets 152 of the push-pull rod 150, as is previously described in FIG. 17.

Also, the lateral lamellas 323 of the internal tube prevent the distancing of elements 346 from the midline, not allowing thus the disengaging of the fastening over the proximal portion 155 of push-pull rod 150, as the drive rod 340 migrates towards proximal.

Detachment of the clamp 100 from the elongated shaft 80 goes through these events in reversed order to those listed above. From the coupling illustrated in FIGS. 16,17, with the rotation of the external tube 300 by 90 degrees in relation to internal tube 320, the unscrewing of the lamellas 310 from sockets 120 of insertable framework is achieved, thus releasing the clamp.

Thus, the lamellas 310 delimit a slot with a long horizontal axis, allowing the proper detachment of the insertable frame 107, of the locking fold 130 in a closed position, of the unlocking element 140 and push-pull rod 150.

Fold 130 is forced to pivot around axis 125 and to close on push-pull rod 150 when it moves through the delimited slot by the two oblique lamellas 310, 310', because, in the opened position, it has a height which does not allow its crossing. Thus, the blocking of push-pull rod 150 in its given position in relation to the fixed elements of the clamp is acquired, leading to the blocking of the forceps arms 101, 102.

Drive rod 340 passes the internal tube 320, pushing the clamp push-pull rod 150 in the same direction by surface 342 applied to the proximal portion 155 of clamp 100. At the same time the elements 346 of the fastening mechanism of clamp's rod 347 are disengaged from sockets 152 of the rod by engaging the trapezoidal edge of the prominent surface 330, being pushed laterally.

By urging the locking flap 130 into the closed position, this will push through its edge 126 of the lateral surfaces of flap, the unlocking element 140 towards the proximal loosing the direct contact with it. It is desirable that the movement toward distal of the drive rod 340 to be made simultaneously with the unscrewing of the frame 107 from lamellas 310 of the external tube 300.

Figure 20:
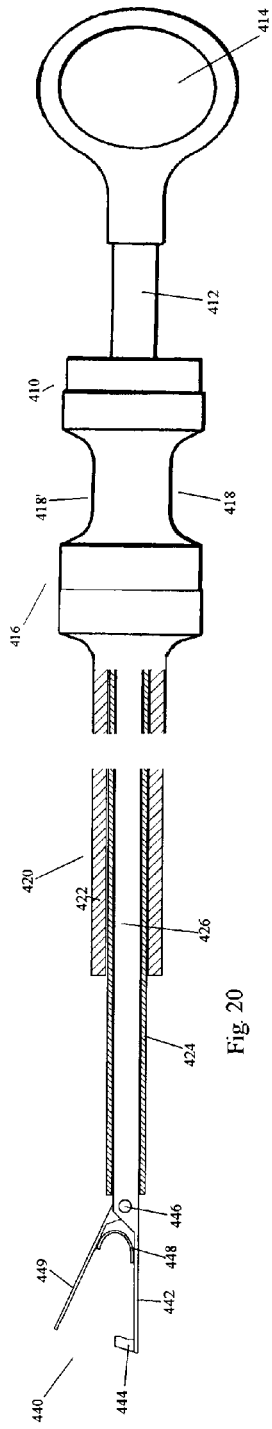
FIG. 20 Side view of the clamp's retrieving device.

FIG. 20 illustrates a side view of a retrieval instrument 400 of the clamp 100. The retrieving instrument 400 comprises a handle 410, an elongated shaft 420 and a prehensile element 440.

The elongated shaft 420 consists of two sheaths, a fixed external one 422, that is circumscribing an internal sheath 424, that is mobile, lengthwise crossed by a rod 426, which continues to its distal termination with prehensile element 440. This one, consists of an immobile arm 442, which continues the axis of rod 426 and presents a hook 444 at the distal termination, and at the proximal termination an axle 446 around which the mobile arm 449 pivots.

Prehensile element's arms are maintained in opened position by an elastic lamella 448 interposed between arms 442 and 449. The handle 410 consists of a plunger 412 which shows in its proximal part, a ring 414, in which the operator's thumb is inserted.

The plunger 412 enters the solid portion 416 of the handle which presents two lateral sockets 418, 418' in which the operator's index and medius fits. In this way, the handle is gripped similarly to a syringe. By pushing the plunger 412 toward distal, similar sliding of the internal sheath 424, toward distal, is achieved.

Figure 21:
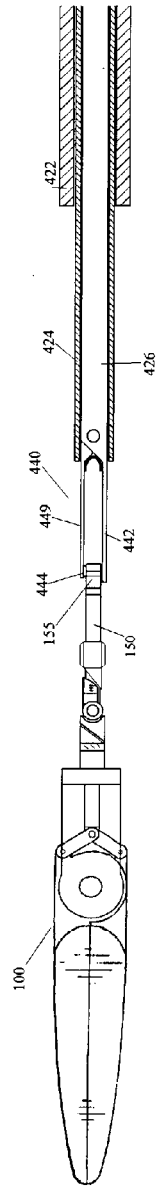
FIG. 21 Side sectional view of the retrieving device's grasp of the clamp.
Figure 22:
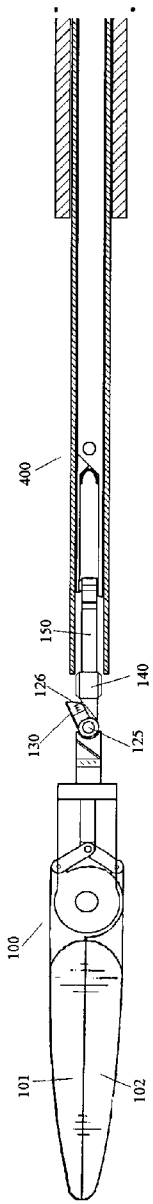
FIG. 22 Side sectional view of the retrieving device's grasp of the clamp.
Figure 23:
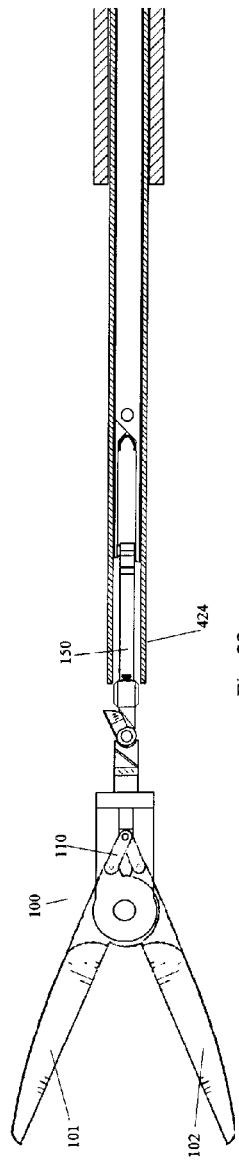
FIG. 23 Side sectional view of the retrieving device's grasp of the clamp.

FIGS. 21, 22, 23, illustrate the operation mode of the retrieving device, in order to extract the intracorporeal applied clamp.

By pressing the plunger 412 in relation to the solid part 416 of the handle 410 (FIG. 20), the correspondent sliding of the internal sheath 424 is made in relation to external sheath 422 and central rod 426, these being attached to the solid portion 416 of the handle.

End tool 100, having the characters described above, is applied as an intracorporeal clamp during a surgical intervention. In order to extract it from the body, the hook 444 located at distal termination of prehensile element 440 of the extractor instrument is inserted into the hole 157 (FIG. 5) located on the proximal portion 155 of push-pull rod 150.

By pressing the plunger 414, the sliding of the internal sheath 424 is made, in relation to rod 426 and consequently to the prehensile element 440, resulting at a first-time the closing of the mobile arm 449 on the fixed arm 442, and thus providing a fixed grip on the distal portion of push-pull rod 150, as appears in FIG. 21.

FIG. 22: subsequent sliding toward distal of plunger 414 performs in the next phase the alignment of the axis of the clamp 100 to the one of extractor device 400 and the engaging of the proximal portion of unlocking element 140, with pushing it toward distal to engage the locking fold 130 at its proximal curved edge 126. The elevation of the blocking flap 130 from push-pull rod 150, by overturning around axle 125 is realized in this way. The result is the unlocking of forceps' jaws 101,102 of clamp 100.

FIG. 23: the additional distal sliding of internal sheath 424 will achieve the opening forceps' jaws 101,102 by pushing towards distal the framework of clamp 100, in relation to push-pull rod 150, releasing thus the clamp from the tissue which was grasped by it, and extracting it from the body.

Thus, a clamp extraction mechanism is performed in a similar manner to the one applied in "opened" surgery, allowing the application of ligations to blood vessels, and knot tying to be made simultaneously with clamp extraction.

FIG. 24 presents a sectional view of the handle, housing from the embodiment illustrated above. It shows handle 30, housing 20, and an elongated shaft 80, attached to the housing via a rotating assembly 50. Handle arm 31, proximally located, has been described above, being fixed to housing 20.

Distal arm 38 of the handle is mobile, being articulated by pivot 40 to housing 20 of instrument 1. On the distal surface of the orifice 39 there is a fold 41, which, in the figure is pushed distally by the operator's fingers in an extension movement of the hand, turning around pivot 42 and acting as a lever through its extension 54, raising thus (applying on inferior surface 74 of curved rod 70), the surface 76 of the rod 70 with teeth 78 from the indentations 53 provided on arm 38. This unlocks the ratchet mechanism 65 and allows free movement of the arm 38 of handle 30 in relation to the fixed arm 31.

It is also showed the locking mechanism 47, which, manually operated at its distal end will allow the fastening of transversal stick 45 located at the lower extremity of fold 41 by socket 49. Thus, the curved rod 70 is maintained elevated with ratchet 65 teeth kept disengaged, thus, allowing permanent free movement of the mobile arm of the handle 38.

Housing 20 of the endoscopic instrument, is articulated with mobile handle arm 38 by pivot 40, the arm 38 engaging through its extension 11 the push-pull rod 12 located inside the housing, at a vertical orifice 13 of it.

The push-pull rod 12 which crosses centrally the housing 20 is articulated at the site of the rotating assembly 50 through a cylindrical articulation 15 with the drive rod 340, which longitudinally crosses the elongated shaft 80, transmitting the controls of the operator, and setting in motion the forceps jaws.

Thus, the closing of the handle arms will lead the push-pull rod 12 to make a translational movement towards distal, and to the closing of the clamp's jaws, and their opening will lead the rod toward proximal. The proximal side of the housing 20 presents a metal stick 57 meant for the application at this level of a monopolar electrode for the inclusion of the device in an electrical circuit, transmitting the electrical current through wire 58 to the push-pull rod 12.

Within its distal portion, the housing is engaged to rotating assembly 50, which also engages distally with the elongated shaft 80. Elongated shaft 80 consists of two tubes, an external tube 300, circumscribing the internal tube 320, there, being a cleavage plain provided between the two tubes, which allows the free rotation of the external tube in relation to the internal one. Centrally, the internal tube is routed by the drive rod 340.

Rotating assembly 50 comprises two segments, an external one 60, having a frustum shape, on which the external tube 300 of the elongated shaft 80 is fixed, the external segment 60 not being attached to the internal tube 320. Portion 60 of the rotating assembly presents on the surface outstanding knobs for the facilitation of manipulation, and is articulated (rotational) to the housing 20 through articulation 62, located at the distal edge of the housing 20.

The rotating assembly 50 presents a second segment 90, having a cylindrical shape, set within the housing 20, movable in relation to the first one in sense of proximal displacement. The internal segment 90 is mobile articulated with the internal tube 320 of the elongated shaft at the level of some fins 84, with a longitudinal long axis, which are inserted into correspondent internal sockets 82 of the cylinder 90.

External segment 60 of the rotating assembly 50 engages with the internal segment 90 through a number of rods 64, originating from the proximal surface of the external segment 60, and entering into the appropriate sockets 63 located on the distal surface of internal segment 90.

In this configuration the two segments of rotating assembly are engaged and set in motion in the same direction by turning the external segment 60 at its outstanding knobs, making an according rotation of the internal and external tubes of the elongated shaft. At the distal extremity of the elongated shaft we find the clamp-shaft coupling shown in FIGS. 16, 17.

Internal cylinder 90 rotationally revolves inside the distal portion of the housing 20 (this having a circular shape on cross-section in its distal portion), under the influence of the movements engraved to external segment 60 of the rotating assembly 50. Internal cylinder shows on its lateral surface, the proximal prominences 75 which enter into corresponding longitudinal notches 97, located on the internal surface of the housing when the cylinder is pulled toward proximal by the trigger assembly 85.

Trigger assembly 85 is manually operated, and enters the housing 20 through a longitudinal slot 87 located on the inferior surface of the housing. Here it is continued with a circumferential collar 95 that is inserted in a circumferential recess 79 located on the outer surface the internal cylindrical segment 90 allowing thus free rotational movement of it.

With the manual pulling of the trigger assembly 85 toward proximal we will obtain the coupling of the rotating assembly 50 illustrated in FIG. 25.

Following the direction of the trigger assembly 85 through collar 95, the internal cylinder 90 of the rotating assembly will be pulled toward proximal with it disengaging from the external segment 60, by rods 64 extraction from their correspondent sockets 63.

The prominences 75 are received into sockets 97 (in this figure they are not all shown) of the housing 20, thus blocking the internal cylindrical segment's 90 rotation in its given position.

In this way, the rotation of external segment 60 by 90 degrees will no longer be transmitted to the internal cylinder, respectively to the internal tube 320 which remain fixed in rotational sense, leading only to the according rotation of the external tube 300, leading to the clamp unscrewing and locking of its jaws while detaching from the elongated shaft, as illustrated in FIGS. 18, 19.

FIG. 26 reveals another preferred embodiment of clamp 500.

Forceps jaws 101,102, the external frame 103 show the same specifications as described in FIG. 5, thus viewing the upper jaw 101 of the forceps, which continues proximally with cylindrical segment 180, viewing its top surface 172, which is articulated at its prominence 174 with lever 110. Lamellas 114 are bilaterally including prominence 174 being attached to it by an axle 115. Parallel with the cylindrical segment is viewed the lower portion 176' of forceps' cylindrical segment of the opposite side and prominence 174', the articulation with lever 110' being of similar making. Note the frame 103 with two parallel arms 102, which include sideways the cylindrical segments 180 and 180' of the forceps jaws, being attached to them at the center axis 105, around which the jaws overturn, being driven by levers 110, 110'. Levers pivot around the axle 185, which runs in a recess located on the inner side of frame arms 102 (FIG. 7), and is anchored to the narrowed distal end 251 of push-pull rod 250, which crosses through the center of the transversal part 106 of frame 103.

Further proximally, is the insertable frame 507, which is attached to the transversal part 106 of external frame 103, of cylindrical shape, and presenting on its surface a thread 508 with several rounds, for screwing into the distal part of the elongated shaft. This frame is also centrally routed by push-pull rod 250 described above. Attachment of the blocking flap 160 to frame 507, is made by a lamella 168, allowing the elevation of blocking flap 160 from push-pull rod 250. The blocking flap 160 comprises an upper surface 162, which connects the two side surfaces 164, attached to slide 168. The top surface presents two upper prominences 165 with the longitudinal shape of an ellipse segment, and rectangular in cross-section, located symmetrical in relation to midline. Side surfaces have a rigid proximal portion 164 which is to be engaged by the wedged portion 142 of unlocking element 140 when pushing it to the distal, elevating flap 160 from push-pull rod 250, thereby allowing its free movement. In the distal side of flap lateral surface, separated from the rigid part 164, there is a flexible lamella 264. Unlocking element 140 has the same constructive characters as described above. The proximal segment of push-pull rod 250 has two symmetrical sockets 252, bordering the proximal portion 255 of push-pull rod 250, this presenting a polycyclic outline with a central hole 258.

FIG. 27 shows a side view of the embodiment of the clamp 500 illustrated above. Forceps arms 101,102 consist of a gripping portion 170, 170', which continues with their according cylindrical segment 180. This is attached to frame 103 (Figured transparent) by pivot 105, which allows the forceps jaws overturning, these being trained by levers 110, 110', which are in turn mobilized by the push-pull rod 250, which is pulled or withdrawn by its proximal portion and centrally traverses from proximal to distal unlocking element 140, locking flap 160, frame 507, and the transversal portion 106 of external frame 103. If it is pushed, the rod leads to the closure of the jaws 101, 102 and with traction to their opening, force being transmitted along the levers 110.

The frame 507 presents at the level of the inferior surface of push-pull rod 250 an extension 509, which acts as a barrier for the unlocking element 140, blocking its excessive pushing towards distal, in this case existing the risk of fracturing the lamella 168.

The locking flap 160 is attached to frame 507 by an elastic lamella 168, which allows the elevation of the blocking flap 160 off push-pull rod 250. Push-pull rod 250 presents along its lateral side an edge 256.

The locking flap 160 presents a superior surface, and two side surfaces 164. The superior surface has two outstanding knobs 165. The side surfaces present a rigid proximal portion 164 with a curved edge 166, which is to be engaged by wedged portion 142 of unlocking element 140 in case of its pushing towards distal, elevating flap 160 off push-pull rod 250, permitting thus its free translation movement. In the distal part of flap's 160 side surface, apart of the rigid part 164, is another surface, this time a flexible lamella 264, with its curved inferior part 266, realizing thus a clamp mechanism around edge 256 of push-pull rod 250, in order to maintain a solid grip. The proximal part of push-pull rod 250 has the same elements as those described in previous figures.

Unlocking element 140 presents a proximal area, that circumscribes the push-pull rod 250 and a triangular distal area, located laterally to the rod which presents the oblique surface 142. It aims to catch on, when the unlocking element 140 is pushed toward distal, the locking fold 160, at the proximal edge 166 of the lateral rigid surface 164, thus, forcing the fold to elevate and release the push-pull rod 250.

Figure 28:
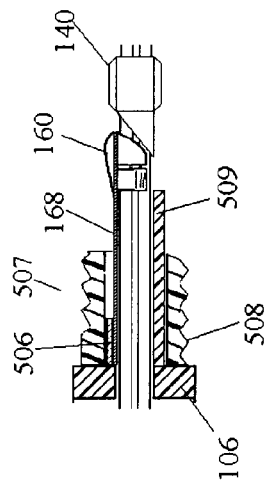
FIG. 28 Side sectional view of the clamp's framework in this embodiment

FIG. 28 illustrates a sectional lateral view of the clamp's framework in the embodiment shown in the two previous figures.

The push-pull rod 250 is being visualized, that centrally crosses from the proximal toward distal the unlocking element 140 (described above), the locking fold 160, illustrated in the closed position, the insertable frame 507, cylindrical, with a thread 508 on its external surface, attached to the transverse portion 106 of the external frame by an extension of it 506, having an asymmetrical form and being inserted within the insertable frame.

To the upper surface of the frame 506 is attached the lamella 168 of the locking fold 160, and the lower surface 509 is greater in thickness and length, exceeding the insertable frame 507 toward proximal, having the purpose of blocking the excessive advancement of the unlocking element 140 toward proximal.

Figure 29:
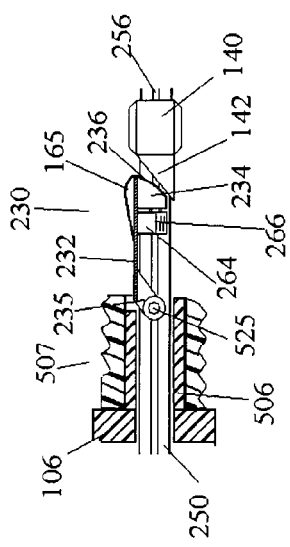
FIG. 29 Side sectional view of the clamp's framework in another embodiment.

FIG. 29 presents a side section view of the clamp's framework 500 in another embodiment. Figured is the locking fold 230 (built similar with the one illustrated in FIG. 11, 12) that is attached to the frame 507, featured in section, together with the transverse portion 106 of the external frame.

External frame is attached to the internal one by a extension of it 506, centrally crossed by the push-pull rod 250. The locking fold 230, illustrated in closed position, consists of a horizontal surface 232, which shows in its distal part two vertical rings 235, which engage and pivot around symmetrical axis 525, oriented toward the inside, from the extension 506, in its proximal portion.

Within the proximal portion of the horizontal surface are present two upper prominences 165. Lateral surfaces of the fold are formed of a proximal rigid portion 234, presenting a proximal curved edge 236, which will be elevated together with the fold by acting of the unlocking element 140 toward the distal.

Within the distal portion of lateral surface, separated from the rigid surface 234 there is a flexible slide 264 having its inferior part 266 curved, acting as a clamp which maintains the locking fold 230 in the closed position, by sliding over the edge 256 of push-pull rod 250, the distance between the two edges being greater than the distance between the tip of the curved segments 266, 266'.

Figure 30:
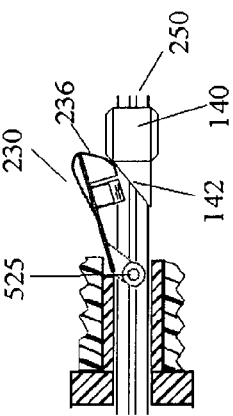
FIG. 30 Side sectional view of the clamp's framework in another embodiment

FIG. 30 presents a side-section view of the clamp's framework shown in the previous figure having the locking flap 230 opened. The unlocking element 140, is pushed distally, and engages by the wedged portion 142 the curved edge 236 of the fold 230, accomplishing the elevation of the locking fold from the push-pull rod 250 by pivoting around the axis 525. Thus, the unlocking of the push-pull rod 250 is performed.

Figure 31:
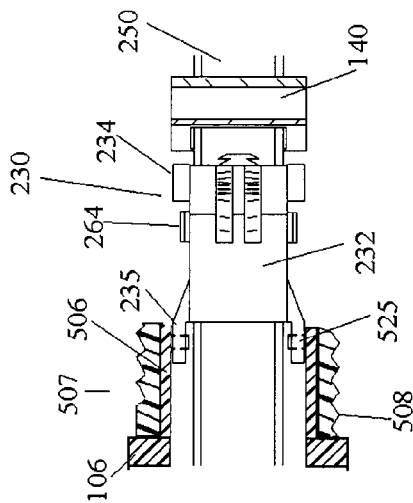
FIG. 31 Superior sectional view of the clamp's framework in another embodiment.

FIG. 31 presents an top section view of the clamp framework shown in previous FIGS. 29, 30. Note the push-pull rod 250, which crosses centrally the unlocking element 140, the locking fold 230, which is pivoting around axis 525, this being anchored on the internal surface of the framework 506.

The locking fold 230, in the closed position, consists of a horizontal surface 232, which presents in the proximal portion of two upper prominences 165.

Figure 32:
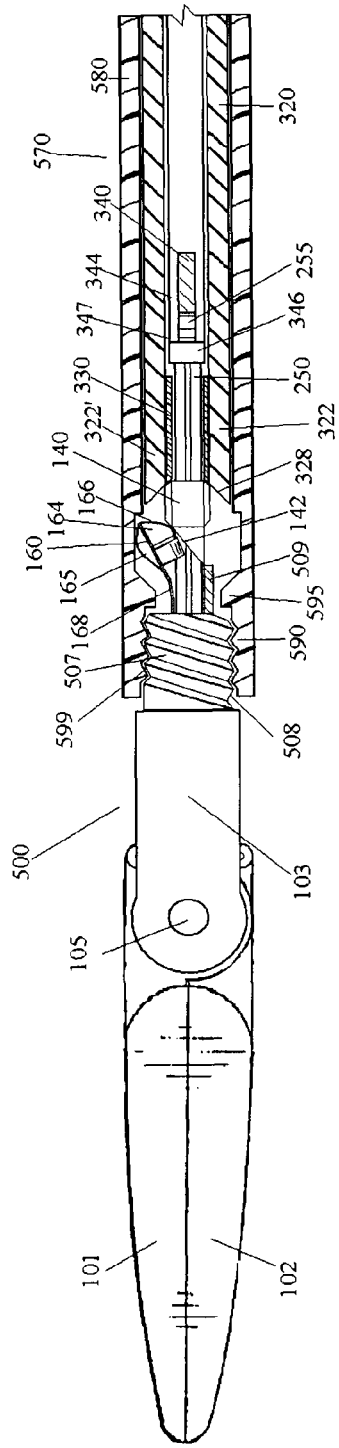
FIG. 32 Side view partially sectioned of clamp-elongated shaft coupling in this embodiment.

FIG. 32 presents a side section view of the clamp-elongated shaft coupling. Clamp 500, as previously described, presents the forceps jaws 101,102', which are pivoting around axis 105, this being fixed to the external frame 103. Transverse portion of the external frame is continued with the insertable frame 507, described above, being centrally crossed by the push-pull rod 250.

The frame 507, having a cylindrical shape, presents on its surface a thread 508 with several coils in order to be screwed into the external sheath of the elongated shaft 570.

Locking fold 160 is in elevated position, lateral surfaces presenting a rigid proximal segment 164 with an curved edge 166, which is to be engaged by the portion 142 of the unlocking element 140. This happens due to its pushing towards distal, when contacting the terminal oblique surfaces 328 of the arms 322,322', by screwing the insertable frame into the external tube 580, thus, elevating the fold 160 from the push-pull rod 250, and allowing its free movement of translation.

Frame 507 presents under the lower surface of push-pull rod 250 a rectangular extension 509, which is acting as an barrier for the unlocking element 140, blocking its excessive pushing toward distal, there, being a risk, in this case of fracturing lamella 168. The proximal part of the push-pull rod 250 has the same elements as those described in previous figures.

Elongated shaft 570 comprises an external tube 580 that circumscribes the internal tube 320 and exceeds it toward distal, there being provided a plane of cleavage between the two tubes, which allows free rotation of the external tube in relation to the internal one.

At the distal portion of the external tube 580, this one presents to the inside the clamp fastening mechanism 599 composed of a thread 590, which, by rotating the external tube 580 relative to the internal one 320 and the clamp 500, is screwed into thread 508 located on the outer surface of the insertable frame 507, thus making the fastening of the clamp to the elongated shaft.

Proximally from the thread 590, the external tube is provided with a collar thickening 595, which delimits a narrower space inside, having the purpose to apply the locking element 160 on push-pull rod 250, when detaching the clamp, in order to block the movements of the forceps arms 101, 102.

Internal tube 320, which has the same specifications as described in FIG. 15 ends proximally to the external one, showing terminally two oblique surfaces 328, 328', which, on one hand allow an easy introduction of push-pull rod 250, delimiting a slot with transverse diameter corresponding to its thickness, and on the other hand engage with proximal portion 148 of the unlocking element 140.

The unlocking element 140 is pushed toward distal when inserting the clamp 500 into the elongated shaft 570. Drive rod 340 centrally crosses in longitudinal manner the internal tube 320, on it being attached the lamella 344, which ends in the element 346, which clings on the proximal portion of push-pull rod 250.

When pushing the drive rod 340 toward distal, it will transmit the force toward push-pull rod 250 of the clamp, and by pulling, the force will be transmitted through the fastening mechanism 347, which does not permit the escape of proximal portion of push-pull rod 250.

Figure 33:
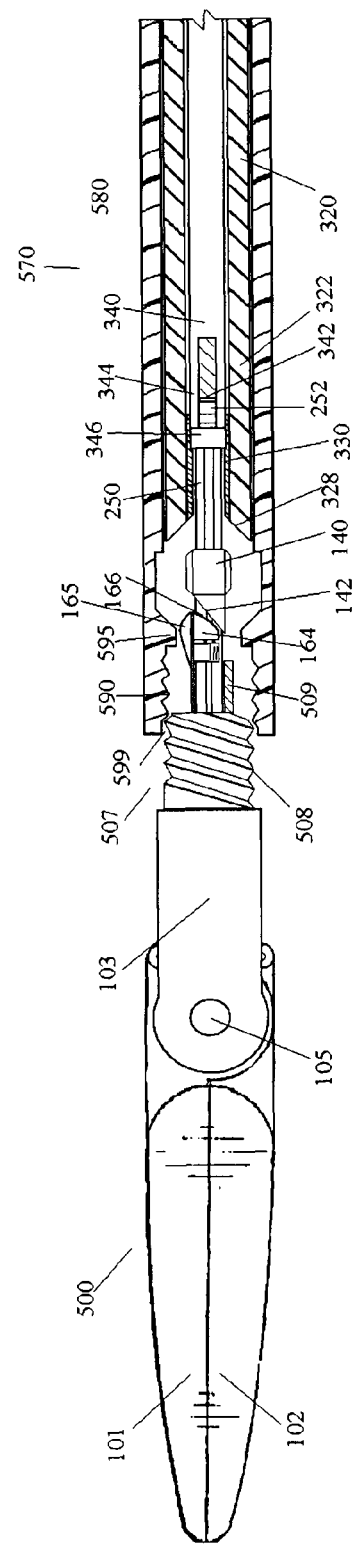
FIG. 33 Side view in section of clamp-elongated shaft coupling in this embodiment at the time of clamp detachment FIG. 34 Top view of an another clamp embodiment FIG. 35 Side view of another clamp embodiment FIG. 36 Side view of another clamp embodiment FIG. 37 Side section view of clamp's framework in an this embodiment FIG. 38 Cross-section view through the clamp's framework.

FIG. 33 shows a side section view of the clamp-elongated shaft coupling when detaching/attaching the clamp.

Clamp 500, as previously described, presents the forceps arms 101, 102', which are swinging around axis 105, this being fixed of the external frame 103.

Transverse portion of the external frame continues with the insertable frame 507, this and the locking fold 160 described above, being centrally crossed by the push-pull rod 250, and leaving, in this order the distal portion of the elongated shaft by the unscrewing of the thread 590 of the clamp fastening mechanism 599 located on the internal end surface of the external tube 580, from the thread 508 of insertable frame 507.

The blocking element 160 is forced to be applied on push-pull rod 250 with the consecutive blocking of its translation movements, by the traversing of the blocking element 160 (previously in elevated position) of the narrower space of collar 595, which engages knobs 165, symmetrically located on the superior surface of the horizontal surface of blocking flap. The side surfaces present a proximal rigid surface 164 with a curved edge 166, which push unlocking element 140 proximally. Thus it is accomplished the blocking of the push-pull rod 250 in the given position at the moment of extraction related to fixed elements of the clamp, and blocking of the forceps' jaws 101,102, arising from this the clamp function of the forceps detached from the elongated shaft.

The drive rod 340 centrally traverses the internal tube 320 towards distal pushing push-pull rod 250 of clamp 500 in the same way, by surface 342 applied on proximal rod segment 255. At the same time elements 346 disengage off recesses 252 of the rod by clambering the border of the prominent surface 330, being pushed to the side.

It is desirable that the movement to distal of drive rod 340 to be done simultaneously with the unscrewing of frame 507 off thread 590 of the external tube 580.

The insertion of clamp in the elongated shaft, passes through the same stages in backward order as previously described, reaching to the configuration described in FIG. 32 with the mention that when introducing clamp, flap 160 must be in closed position, to be able to traverse the narrowing of the external tube given by the collar 595.

The retrieving of the clamp 500, applied intracorporeal will be done with the same instrument, and passing through the same stages as the ones described in FIGS. 20,21,22,23.

In this embodiment, housing 20, handle 30 and rotating assembly 50 have the same characteristics as the ones illustrated in previous example on FIGS. 24,25 having as a difference, the fact that, for detaching, respectively attaching clamp 500 to the elongated shaft 570 more rotation turns are needed at the level of the external segment 60 of rotating assembly 50 with the internal segment 90 hauled to proximal by trigger assembly 85, achieving thus unthreading, respectively threading of the clamp to the elongated shaft on level with the fastening device 599.

In FIG. 34 is featured another embodiment of the clamp in top view, in functional position, the modality of blocking the rod changing in comparison with the previous examples. The clamp 600 comprises the forceps' jaws 101, the external frame 103, with its transversal portion 106, this being attached to the cylindrical insertable frame 607, which proximally presents the extension 383 of the unlocking element 380, all these being centrally traversed by push-pull rod 350. The push-pull rod 350, of rectangular shape, having the horizontal transversal diameter longer than the vertical one, proximally presents two triangular side recesses 352, 352', which border proximal segment 355, by which the rod's mobilization is accomplished. Segment 355 of the rod also presents a vertical orifice 358, on which the retrieving instrument is applied. On side surfaces, the rod presents some indents 357, with the purpose of blocking the rod in a certain position in proportion to the longitudinal axle, around which it can rotate. In the distal part, inside the frame 103, the rod ends on circular section, in a cylindrical articulation 360, received by frame 367, which continues with an extension 368, interposed between levers 110,110', on which axle 185 is inserted. This is transmitting the movement to levers 110, 110', mobilizing forceps' jaws. The wider portion of cylindrical articulation 360 has the purpose to also engage and push lever 110 towards distal, increasing thus the force which will be transmitted for the closing of the forceps' jaws.

The forceps' jaws 101,102, the external frame 103 present the same assembling manner as the ones described in FIG. 5, thus viewing the superior arm 101 of the forceps, which proximally continues with its cylindrical segment 180, viewing its superior side 172, which articulates on its knob extension 174, with lever 110, being fixed to it by an axle 115. In parallel with the cylindrical segment, the inferior portion 176 of the cylindrical segment of forceps' jaw of the opposite side is visualized, and knob 174', the articulation with lever 110' being made in similar way. It is observed frame 103 with its two parallel arms 102, which bilaterally include cylindrical segments 180 and 180' of forceps' jaws, in their centre passing axle 105, around which they overturn, being driven by levers 110,110'. These pivot with their proximal portion around axle 185, which runs through a recess located on the internal surface of frame's arms 102 (FIG. 7), and is anchored by the distal extremity 368 of cylindrical articulation 360, which articulates with the distal part of push-pull rod 350.

Proximally is the insertable frame 607, which is attached to the transversal part 106 of the external frame 103, of cylindrical shape and presenting on its outer surface a thread 608 with several coils, in order to be screwed in the distal part of the elongated shaft. In the proximal half, the insertable frame has no thread, and the proximal circular extremity has some indents 603 which have a purpose in extracting the clamp 600. From the inside of the proximal portion of cylindrical frame 607, comes out towards proximal the extension 383 of the locking element of rotation 380, applied on the superior surface of push-pull rod 350, the terminal surface having a oblique orientation 385.

FIG. 35 presents a side view of the version of the clamp 600 previously illustrated, with push-pull rod 350 in functional position, having the long transversal axle horizontally oriented. Forceps' jaws 101,102 are formed of a portion with prehensile purpose 170,170', which continues with its corresponding cylindrical segment 180. This is attached to frame 103 by pivot axle 105, which permits the overturning of forceps' jaws around it, they being trained by levers 110,110'. These are being mobilized by push-pull rod 350 through cylindrical articulation 360, the rod being pushed or redrawn in its proximal portion 355 and centrally traverses from distal to proximal the external frame 103, its transversal part 106, and the insertable frame 607. From the inside of frame 607, emerge the extensions of the blocking element 383, 383', applied on superior and inferior surfaces of push-pull rod 350. The rod trains in case of its pushing to distal the closing the of the forceps arms and in case of its drawing towards proximal their opening by transmitting the force along levers 110.

FIG. 36 presents a side view of clamp 600, with the push-pull rod 350 blocked, this having the transverse long axis vertically oriented. The constructive elements are similar to those illustrated in the previous figure, the difference being given by the rotation of push-pull rod 350 around its longitudinal axle, so that it traverses the insertable frame 607, respectively the transversal part of the external frame with the long transversal axis in vertical position. Push-pull rod 350 presents on side surfaces now vertically oriented, indentations 357, with the purpose of blocking the rod in its position in relation to the longitudinal axis, around which this can rotate. In the distal part, included by frame 103, the rod ends in a cylindrical articulation 360, engaging it with its terminal portion 365, circular in section and rotated to 90 degrees in relation to frame 367, which cannot rotate. The frame 367 continues with an extension 368, through which the movement is transmitted to levers 110,110' mobilizing the forceps' jaws. Also, from the insertable frame 607 emerges the prominent proximal extension 383 of locking element of the rod's rotation 380 (FIG. 37) which is also rotate together with push-pull rod 350.

FIG. 37 presents a side sectional view of the clamp's 600 framework, in the embodiment exposed in the three previous figures. The push-pull rod 350, having the transversal horizontal diameter longer than the vertical one, proximally presents side recess 352, which border the proximal segment 355. On side surfaces, the rod presents indentations 357, with the purpose to block the rod in a certain position in relation to the longitudinal axle, around which it can rotate. In the distal part, the rod ends in a cylindrical articulation 360, in which the terminal portion of rod 365, on circular section is engaging, with frame 367, as previously described.

In the distal half of insertable frame 607, that is provided with a thread 608, are located on the internal surface, superior and inferior, several indentations which form the blocking element 612, horizontally oriented, on transversal section having the shape of a circle segment, which are to be engaged with teeth 357 located on the side surfaces of push-pull rod 350 at the moment that this is rotated with the long transversal axle in vertical position. In this figure, the rod is in functional position with the long transversal axle horizontally oriented, so that free translational movements of it are allowed. The non-threaded proximal portion 609 of the insertable frame 607, is also cylindrical, presenting on its terminal border a crown of teeth 603 with purpose in extracting the clamp. Inside it, pushed towards proximal by a spring 615, is located the blocking element of the rod's rotation 380, also of cylindrical shape, presenting proximally an extension 383, 383', applied on the superior, respectively inferior surface of push-pull rod 350, which surpasses the border of frame 607.

At the base of the extensions 383,383' is a set of teeth 381,381', which are to be engaged with another set of indentations 610, in crown disposal and prominent on the internal terminal surface of frame 609. The blocking element of the rotation is pushed in proximal position with teeth 381,381' engaged with the internal indentations 610 of frame 609 by spring 615, which proximally applies on blocking element 380, and distally on the threaded portion 608 of frame 607, narrower in the internal diameter than portion 609. In this way, the accidental rotation of push-pull rod 350 is prevented, respectively blocking/unlocking of the translation movements of the rod. The only way in which the blocking element can be passed from the position of blocking the rod to the position of unlocking it, or vice-versa, is to push towards distal the extensions 383, 383' of locking element 380, with consecutive disengaging of teeth 381,381' from indentations 610.

FIG. 38 shows a sectional transversal view through clamp's framework, illustrated in the previous figure at the level indicated by the arrows. It is illustrated the insertable frame 607, presenting on its surface a thread 608 and on the interior surface blocking element 612, represented by superior and inferior horizontal indentations of circle segment shape. Push-pull rod 350 is presented with its long transversal axle with horizontal orientation, so the indentations placed on its side surfaces are not engaged with those of the blocking element 612, permitting thus the free movements of the rod.

FIG. 39 shows a side sectional view of the clamp's framework in the embodiment described above, with the push-pull rod 350 vertically rotated. In this way, indentations 357 located on the sides of the push-pull rod 350 engage with horizontal indentations of blocking element 612, blocking the movement of push-pull rod 350. Components are the same as illustrated above, the difference being given by the push-pull rod 350 rotated around its longitudinal axis, ending it in a cylindrical articulation 360, in which its terminal portion 365, circular in section and also rotated 90 degrees engages with the frame 367, not rotated. Also rotated by 90 degrees, are extensions 383 of locking element 380. Note the frame 609 in which the blocking element 380, is rotated by 90 degrees together with the push-pull rod 350 so that the teeth 381 located at the base of its proximal extension, vertically oriented, are engaging with the indentations 610 of frame 609. The rotation lock element 380 is pushed toward the proximal end of portion 609 of insertable frame maintaining thus the engagement between indentations above-mentioned by spring 615, thus stopping the accidental rotation of the rod which could lead to clamp dislodging. It is also visualized the proximal part of the push-pull rod 350, bordered by two sockets 352 on the side surfaces and orifice 358.

FIG. 40 shows a cross-sectional view through the clamp framework shown in the previous figure on the level indicated by the arrow. It is illustrated the insertable frame 607, with thread 608 on its surface and the locking element 612, represented by indentations in the form of upper and lower horizontal circles segments. Push-pull rod 350 is presented with its long transverse axis having vertical orientation, so that arciform indentations placed on its side surfaces engage with the locking element 612, thus blocking the rod moves.

FIG. 41 shows a sectional side view of the clamp-elongated shaft coupling.

Clamp 600, as it was previously described, presents forceps jaws 101,102, overturning around axis 105 which is fixed to the external frame 103. Transversal portion of the external frame continues with the insertable frame 607, described above, centrally routed by push-pull rod 350. Elongated shaft 670 comprises an external tube 680 circumscribing the internal tube 320 and surpassing it distally. Also, there is a cleavage space between the two tubes, which allows the free rotation of the external tube in relation to the internal one and vice versa. At the distal portion of external tube 680, this presents on its inner surface the clamp fastening device 699, consisting of a screw 690, which, by rotating the external tube 680 in relation to the internal one 320, leads to the attachment/detachment of the clamp 600 by threads 608, thereby fastening the clamp to the elongated shaft.

Internal tube 320, which presents the same specifications as described in FIG. 15, is shorter compared to the external one, distally showing two oblique surfaces 328, which, on one hand allow an easy introduction of the push-pull rod 350, delimiting a slot with width corresponding to its transverse diameter, and on the other hand engage the proximal oblique surfaces 385, 385', of proximal extensions 383 of the rotation locking element 380 of push-pull rod 350, which show the same slope. Locking element 380 is pushed towards distal after the engagement of its proximal extension 385 to the oblique surfaces 328 of the insertable frame 320, when inserting the clamp 600 in the elongated shaft 670 and the screwing of the two, viewing that the spring 615 is being compressed. Also this leads to the disengaging of teeth 381, off indentations 610 located on the insertable framework. This allows the free rotation of push-pull rod 350, respectively the locking/unlocking of its translational movements. Note also the push-pull rod 350 driven with its long transversal axis horizontally oriented, allowing free movement. Drive rod 340 centrally crosses through the internal tube 320, to it being attached to the rod fastening device 347, as previously described. When pushing the drive rod 340 towards distal, it will transmit its force to the push-pull rod 350 of the clamp, and by pulling, the force will be transmitted through the slides 344, respectively element 346, which prevents the dislodging of the proximal segment 355 of push-pull rod 350. Internal tube 320 distally ends in two parallel arms 322 each having a prominent proximal surface 330, delimiting a polygonal slot 326 previously described.

FIG. 42 shows a sectional side view of the clamp-elongated shaft coupling, with the push-pull rod 350 rotated in vertical position, thus locking its translational movements. This rotation is accomplished by, and together with the internal tube 320, also illustrated in a vertical position, and is an intermediate stage in the process of attachment, respectively detachment of clamp 600 to/off the elongated shaft 670. Clamp 600, as previously described, presents forceps jaws 101,102, overturning around axis 105, which is fixed to the external frame 103. Transversal portion of the external frame continues with the insertable frame 607, described above, centrally routed by push-pull rod 350, also figured in vertical position. In this way, the indentations 357 of the push-pull rod 350 engage with locking device 612 represented by horizontal indentations applied on the inner surface of the insertable frame 608, blocking the movement of the push-pull rod 350. Components are similar to those illustrated in the previous figure, the difference being given by the rotation of the push-pull rod 350 by 90 degrees around its longitudinal axis. Note, in the proximal portion of the frame 607, the locking element 380 being pushed to the distal, compressing spring 615, by the back-pressure given by the engagement of its extensions 383 to the internal tube 320, when fixing the clamp 600 by screwing into the external tube 680. Locking element is rotated by 90 degrees together with the push-pull rod 350 so that the teeth 381 located at its proximal extension are located in vertical position, and also disengaged from teeth 610 of the insertable frame, thus allowing the rotation of the push-pull rod 350, respectively to lock/unlock the translational motion of the rod.

Elongated shaft 670 comprises an external tube 680, that is circumscribing the internal tube 320, there being a cleavage space between the two tubes, which allow their separate rotation. Internal tube 320 is shown rotated, with terminal arms 322 in vertical position, which present the same specifications as described in FIG. 15, ending in two oblique surfaces 328, that engage the obliquely cut proximal portion 385, of the rotation lock element 380 of push-pull rod 350, which presents the same slope. Inducing a rotational movement to the internal tube will also lead to the consequent turning of the push-pull rod 350, and of the blocking element.

Drive rod 340 centrally routes the internal tube 320, to it being attached the clamp rod fastening mechanism 347. The rod 340 will remain within the internal tube, bordered by the two side fins 323, which do not allow the disengaging of 347 from recesses 352 which border the proximal portion of push-pull rod 350.

FIG. 43 shows a sectional side view of the clamp-tube coupling, at the time of attaching, respectively detaching the clamp. This stage is preceded by the rotation of the rod in a vertical position, as illustrated in previous figure, and in case of attaching the clamp, the sequence of events is reversed (FIG. 43, 42, 41).

In this way indentations 357 located on lateral sides of the push-pull rod 350 engage the locking element represented by the horizontal teeth 612 applied on the upper and lower inner surface of the insertable frame 608, blocking the movements of the push-pull rod 350. This is a necessary condition for detaching the clamp. Locking element 380 is rotated by 90 degrees, together with the push-pull rod 350, so that teeth 381 located at its proximal extension's 383 base lie vertically, engaging with the indentations 610 which are located in crown on the internal proximal edge of the insertable frame. This happens because the lock element's 380 extensions 383 are released from the counter pressure given by the terminal surface 328 of the internal tube 320, while unscrewing the clamp from the elongated shaft. The rotation lock element 380 is pushed proximally, maintaining the engagement between indentations above mentioned by spring 615, thus stopping accidental rotation and skidding of the clamp until the proximal extension of the rotation lock is pushed toward the distal.

Elongated shaft 670 comprises an external tube 680, that is circumscribing the internal one 320. In the distal portion of the external tube 680, it presents on its inner surface the clamp fastening mechanism 699, consisting of a screw 690, which, depending on the direction of rotation of the external tube 680 in relation to the inner one 320, leads to the screwing/unscrewing of the clamp 600 by the thread 608 located on the outer surface of the insertable frame 607, making the attachment of the clamp to the elongated shaft possible.

As described previously, drive rod 340 passes through the internal tube 320, pushing push-pull rod 350 in the same direction through surface 342 applied on the proximal clamp portion 355. Meanwhile, triangular elements 346 are disengaged from recesses 352, after contacting the prominent surface 330, being pushed sideways, as previously described. The clamp is presented with the rod rotated vertically blocking its translational movements.

FIG. 44 shows a sectional side view of the housing and rotating assembly in this embodiment. Constituent elements are essentially the same as those described in FIGS. 24, 25, except recesses 98 located on the inner distal portion of the housing 20 (which replace recesses 97 described above), in this variant of curved form, which are entered by the projections 75 located on the outer surface of internal segment 90 of the rotating assembly 50, when the proximal segment 90 is pulled by trigger assembly 85. With external segments 60 and 90 internal of the rotating assembly 50 engaged, and the trigger assembly 85 being pushed to the distal, as illustrated in the figure, we find the elongated shaft-clamp coupling as illustrated in FIG. 41.

Once with pulling the trigger assembly 85 proximally we obtain the rotating assembly module coupling 50 illustrated in FIG. 45.

Following the movement of trigger assembly 85 through collar 95, the internal cylinder's outer projections 75 will enter into recesses 98 (not seen in this figure) of the housing, which leads to the internal cylindrical segment 90 rotation by 90 degrees relative to initial position. This motion is also induced to the internal tube by sockets 82 in which the lamellar radial extensions 84 of the tube 320 penetrate. At the distal end of elongated shaft result the joining configuration shown in FIG. 42.

Also the disengaging of external segment 60 from the internal one 90 is produced, by extraction of rods 64 off the correspondent recesses located on the distal surface of the internal segment. In this way, the rotation of the external element will not be transmitted to the internal cylinder, respectively to internal tube 320, leading only to the rotation in the same direction of the external tube 680, so to the screwing/unscrewing of the clamp with its jaws blocked at the operating site as it is shown in FIG. 43.

Figure 46:
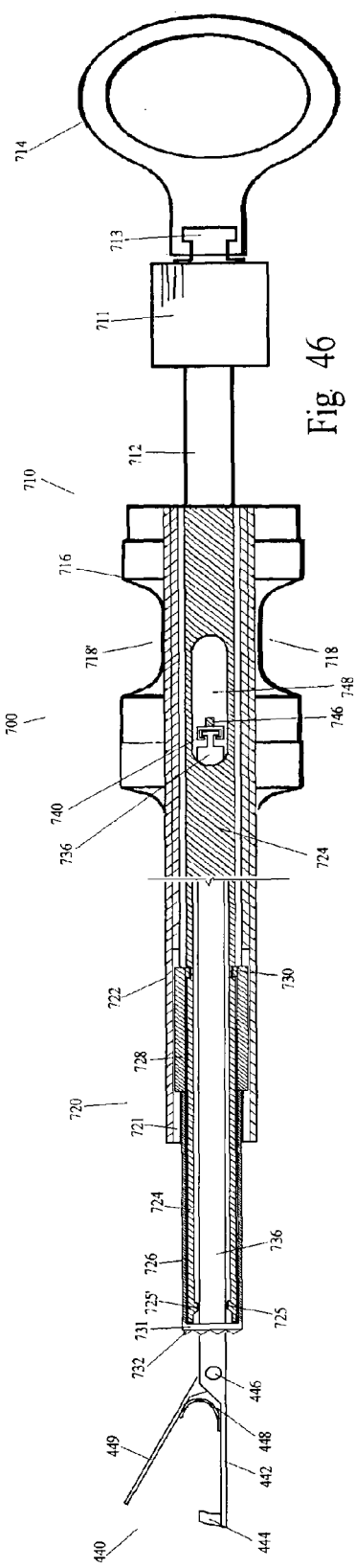
FIG. 46 Side sectional view of the retrieving device

FIG. 46 illustrates a sectional view of a retrieving device of the clamp 700. The retrieving device 700 consists of a handle 710, an elongated shaft 720 and a prehensile element 440.

The elongated shaft 720 consists of three concentric sheaths, an external one 722 fixed to the handle, an internal mobile sheath 724, acted by the plunger, presenting in its distal portion two internal knobs located diametral opposite 725,725'. Between the two sheaths a middle sheath 726 is interposed, which comprises the internal sheath, being rotationally immobile to the external sheath 722 due to of some lamellar radial extensions 728 proximally located, which enter into longitudinal recesses 721, located on the internal surface of the external sheath, which allow thus only the translational movement of the middle sheath in relation to the external one. The middle sheath is also translational immobile in relation to the internal sheath 724, being attached proximally by an internal collar 730, which enters in a circular recess located on the external surface of the internal sheath, and also distally, level on which it exceeds the internal sheath, where it presents a crown 731 with indentations 732 on its distal border, permitting thus only rotational movements between the two mentioned sheaths. The internal sheath is routed by a rod 736, which continues on its distal end with the prehensile element 440. This comprises a fixed part 442, which continues the rod 736 and presents on its distal end a hook 444 and at the proximal end an axle 446 around which the mobile segment 449 pivots. The prehensile element is maintained in opened position by a leaf spring 448, interposed between arms 442 and 449.

The handle 710 presents a plunger 712 with a rotating cylinder 711 in its proximal part, which is articulated by a cylindrical articulation 713 with a ring 714, in which the operator's thumb is inserted. The plunger 712 penetrates in the solid portion 716 of the handle which presents two side recesses 718,718', in which the index and middle finger of the operator are inserted.

The internal sheath 724 is in extension of the plunger 712, and, at the level of the solid portion 716 of the handle, presents an elliptic hole 748. At this level, rod 736 is fixed on the handle, by a transversal bar 746. The attachment of the rod 736 is done by a cylindrical articulation 740, which permits free rotational movements of the rod.

By pushing towards distal the plunger 712, the according gliding of the internal sheath 726 and of the middle one is accomplished, and by rotating the cylinder 711, the according rotation of the internal sheath 726, and the prehensile element 440 is made, along with rod 736, in relation to the external sheath 722 and the medial one 726.

Figure 47:
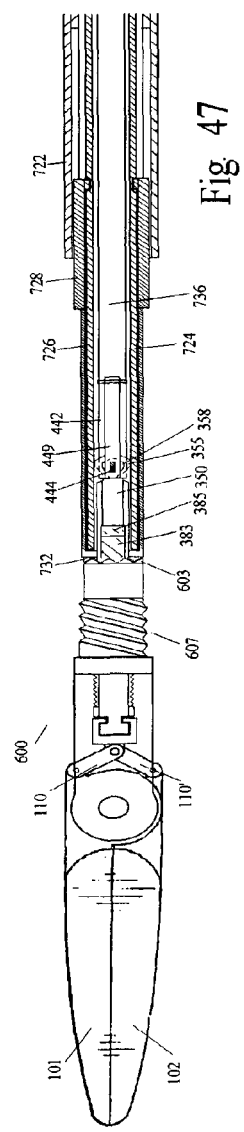
FIG. 47 Side sectional view of the retrieving device's grasp of the clamp
Figure 48:
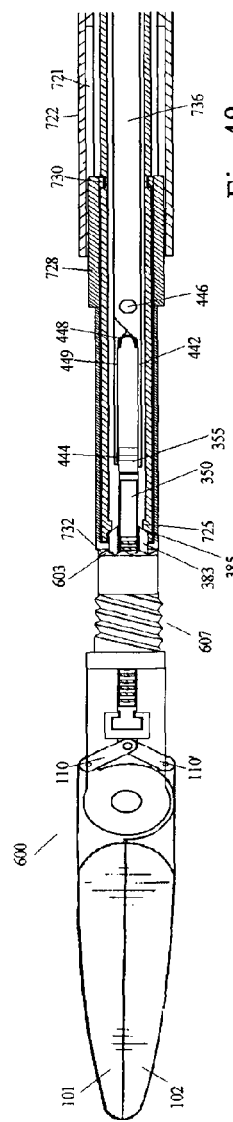
FIG. 48 Side sectional view of the retrieving device's grasp of the clamp

FIGS. 47, 48 illustrate the functional mode of the retrieving device 700, in order to extract the intracorporeal placed clamp 600.

By pressing the plunger 712 in relation to the solid part 716 of handle 710, the according gliding of the medium 726 and internal 724 sheaths is accomplished, in relation to the external sheath 722 and the central rod 726, these being fixed at the level of the handle 716.

The clamp 600, having the characteristics previously described is applied during a surgical intervention, with push-pull rod 350 rotated in vertical position, thus blocking the movements of the clamp's jaws 101,102. To extract it from the body, the hook 444 located at the distal end of prehensile element is inserted in orifice 357 of the proximal segment 355 of push-pull rod 350.

By pressing plunger 714, the according gliding of the internal sheath 724 and medium one 726 is accomplished, in relation to rod 736 and prehensile element 440, resulting at a first time the closing the mobile arm 449 on fixed arm 442 and assuring a fixed grip on the proximal segment 355 of push-pull rod 350. The progressive gilding towards distal accomplishes the alignment of the long axis of the clamp 600 to the one of extractor instrument 700 and the approach of the proximal extension of unlocking element of rotation 383 by the internal knobs 725,725' of the internal sheath with their pushing towards distal. This way, the blocking element 380 of the rotation (FIG. 37) is pushed towards distal, permitting the free rotation of push-pull rod 350. At the same time, crown 731 with indentations 732 is applied on the proximal border of cylinder 607, provided with congruent indentations 603. The rotation by 90 degrees of cylinder 711 the pivoting of the internal sheath 726 and the prehensile element 440 is realized, along with rod 736, related to the external 722 and the medium 726 sheath. Teeth 732 located on the distal border of the medial sheath 726 block the clamp's framework rotation, by engaging with teeth 603, permitting only the rotation of push-pull rod 350, thus unlocked.

The additional gliding of internal sheath 724 with push-pull rod 350 in horizontal position will lead to the opening of the forceps' jaws 101,102, releasing the forceps off the tissue which was grasped by it and extracting it from the body.

It is accomplished thus an extraction mechanism similar to that applied in "opened" surgery, permitting the use of ligatures.

Figure 49:
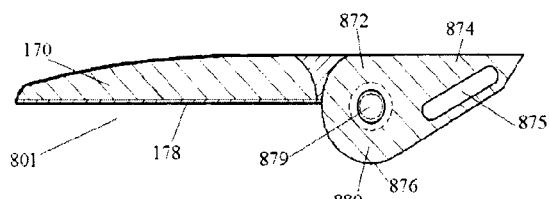
FIG. 49 Side section profile through the upper jaw of the clamp in another embodiment.

FIG. 49 illustrates a side view of an alternative embodiment of the clamp's jaws 801, they presenting a prehensional part 170, with same elements as previously described. Forceps jaw progressively thickens towards proximal, where its segment 880, pivots around the axle introduced in central orifice 879. The segment 880 presents a superior side 872, located in the extension of the jaw and an inferior one 876, progressively narrowing towards proximal by a triangular extension 874 of the same thickness as the portion 880 which presents a elongated slot 875 with oblique orientation.

Figure 50:
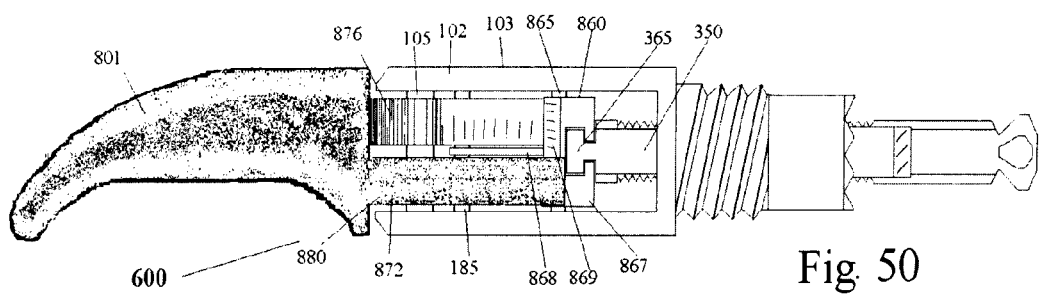
FIG. 50 Top view of another embodiment of the clamp
Figure 51:
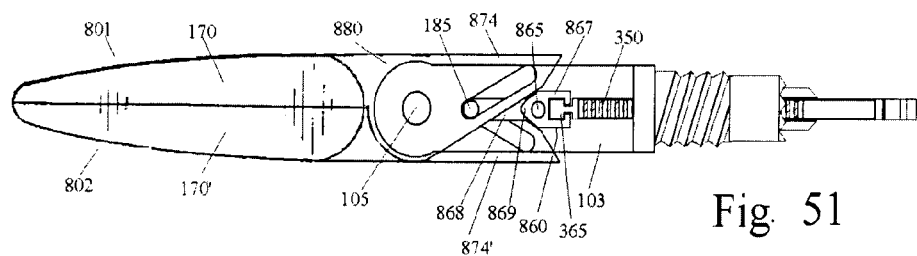
FIG. 51 Side view of a another embodiment of the clamp

FIGS. 50, 51 shows a superior view respectively side view of the clamp 600 in the embodiment of using opposable jaws 801,802 built as illustrated in the previous figure. The forceps' jaws are attached to frame 103 by pivot axle 105, which allows their overturning around it, they being mobilized by push-pull rod 350.

In the distal part, bilaterally included by frame 103, the rod ends in a cylindrical articulation 860 in which the terminal portion 365 of rod engages with a frame 867. The frame continues with a lamellar extension 868, interposed between the triangular extensions 874, from which axle 185 derives, and enters into the slots 875 located in the thickness of extensions 874 and sideways is inserted in the internal recesses of arms 102 (FIG. 7) of frame 103. The distal portion 869 of cylindrical articulation 860 has a semi-elliptic shape on section, having the purpose to engage and push divergently the oblique surfaces of extensions 874,874', thus transmitting an augmented force for the closing of the forceps' jaws. The training the forceps' jaws is made, by divergent pushing of extensions 874 with the progression of push-pull rod 350 towards distal, and their converging in case of pulling towards proximal, by the axle 185 that is inserted in slots 875. At the level of the articulation 860 starts a transversal axle 865, also inserted in internal recesses of arms 102, which gives it stability.

The other constitutive elements of clamp 600 were previously described. Also arms 801,802 can be applied as an alternative embodiment of clamp's construction in the previous embodiments.

Figure 52:
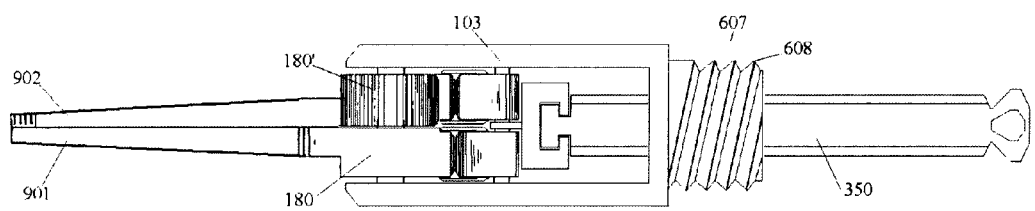
FIG. 52 Top view of an embodiment in which the jaws are represented by scissors.
Figure 53:
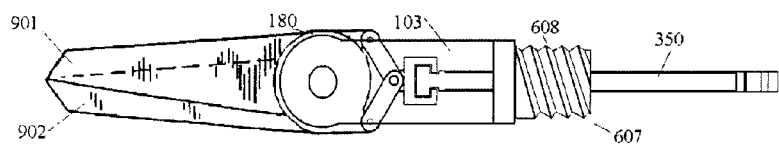
FIG. 53 Side view of an embodiment in which the jaws are represented by scissors.

FIGS. 52 and 53 illustrate a superior, respectively side view of the clamp in an alternative embodiment in which the forceps' jaws are replaced by scissors 901,902. The constitutive elements are the same as the ones described in FIGS. 34,35,36 as concerning the cylindrical segments 180, their engaging with push-pull rod 350, frame 103, except for the insertable frame 607, which is embodied in this version only by the portion which presents the outer thread 608 with the purpose of its screwing in the elongated shaft 670, and push-pull rod 350, which no longer presents indentations on its side surfaces.

Figure 54:
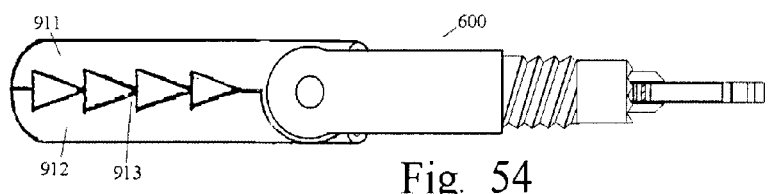
FIG. 54 Side view of another embodiment of the clamp.
Figure 55:
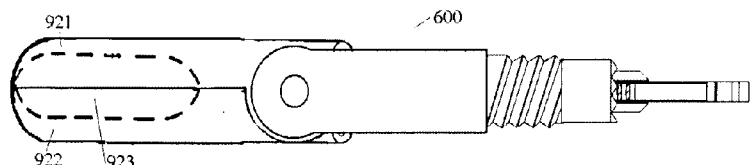
FIG. 55 Side view of another embodiment of the clamp.

FIGS. 54, 55 and 56 illustrate a side view through clamp 600, with opposable jaws of the forceps have shapes that allow them special purposes in a surgical intervention. There are represented the arms of a "crocodile-forceps" 911,912, in FIG. 54, these presenting strong teeth 913 oriented towards proximal, which accomplishes a strong gripping force on the tissue. The opposable arms 921,922 illustrated in FIG. 55 have a shape which delimitates an internal cavity 923 resulting a biopsy forceps.

The invention claimed is:

1. A minimally invasive surgery instrument, comprising:
   a. an end tool that is detachable as a retrievable clamp that includes jaws driven by a push-pull rod, the push-pull rod being included within a framework, the end tool being provided with a locking element that is represented by a specific configuration of said push-pull rod that is presenting a segment with symmetrical opposed teeth, an articulation of the push-pull rod that enables said segment of it to revolve around its axis when detaching said end tool from an elongated shaft, thereby gearing said teeth to another set of teeth located on said framework, b. a handle and elongated shaft part that comprises an elongated shaft comprised of concentric tubes and means for revolving said segment around its axis, said elongated shaft being connected to a rotating assembly, that Is attached to a housing inside which a rod is driven by said handle, c. whereby said handle and elongated shaft part transmits a surgeon's commands leading to the actuation of the clamp's jaws by actuating said handle as long as the end tool is attached to said elongated shaft, as well as clamp deployment from the elongated shaft and reattachment to said elongated shaft, by operating on a coupling given by the movement of said concentric tubes in relation to each other, thus resulting in the detachment of said clamp with said jaws locked in their given position at the time of detachment or an attachment of said clamp to said elongated shaft, which leads to ungearing of said teeth.

2. A minimally invasive surgery instrument, comprising:

a. an end tool that Is detachable as a retrievable clamp that includes jaws driven by a push-pull rod, the push-pull rod being included within a framework, the framework being provided with a flap mechanism that is pushed against said push-pull rod, when detaching said end tool as a clamp from an elongated shaft, said flap mechanism presenting securing means represented by ratchet teeth that engage teeth represented on said push-pull rod, said end tool further comprising an articulating means for coupling said end tool to said elongated shaft, an unlocking element that elevates said flap mechanism upon retrieval of said retrievable clamp to said elongated shaft;

b. a handle and elongated shaft part that comprises said elongated shaft comprised of concentric tubes and means for pushing said flap mechanism against said push-pull rod upon detachment, said elongated shaft being connected to a rotating assembly, that is attached to a housing inside which a rod is driven by said handle;

c. whereby said handle and elongated shaft part transmits a surgeon's commands leading to the actuation of the clamp's jaws by actuating said handle as long as the end tool is attached to said elongated shaft with said flap mechanism kept elevated, as well as clamp deployment from the elongated shaft and reattachment to said elongated shaft, by operating on a coupling given by the movement of said concentric tubes in relation to each other, thus resulting in the detachment of said clamp with said jaws locked in their given position at the time of detachment or an attachment of said clamp to said elongated shaft.

3. A surgical endoscopic instrument with detachable end tool as a clamp, comprising: an end tool that is detachable as a retrievable clamp that includes jaws driven by a push-pull rod and a framework that presents a locking element for said push-pull rod, said locking element being pushed against and presenting means for securing said push-pull rod when detachment occurs, said clamp being removably connected by a coupling to an elongated shaft that comprises two concentric tubes, an internal one, and an external one, which can rotate about each other, tube, longitudinally crossed by an axially moving drive rod with a fastening mechanism for the clamp's push-pull rod, presenting a collar that pushes said locking element upon detachment of end tool, connected to a rotating assembly that is attached to a housing, inside which a rod, driven by a handle, transmits a surgeon's commands leading to the actuation of the clamp's jaws, as well as clamp deployment from said elongated shaft, by operating said coupling given by the rotation of said concentric tubes in relation to each other, thus resulting in the detachment of said clamp with said jaws locked in their given position at the time of detachment or an attachment of said clamp to said elongated shaft, whereby said locking element is being kept elevated as long as said end tool is attached to said elongated shaft.

* * * * *